(12) United States Patent
Zhang et al.

(10) Patent No.: US 11,826,044 B2
(45) Date of Patent: Nov. 28, 2023

(54) SURGICAL STAPLING DEVICE WITH CURVED TOOL ASSEMBLY

(71) Applicant: Covidien LP, Mansfield, MA (US)

(72) Inventors: Jiangfeng Zhang, Shanghai (CN); Xini Zhang, Shanghai (CN); Syed Sarfraz Ahamed, Shanghai (CN); Shunhong Xu, Shanghai (CN); Ping Ren, Shanghai (CN); Manojit Hazra, Hyderabad (IN); Sridharan Varadhan, Shanghai (CN); Zhinan Guo, Shangai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/631,096

(22) PCT Filed: Aug. 2, 2019

(86) PCT No.: PCT/CN2019/099046
§ 371 (c)(1),
(2) Date: Jan. 28, 2022

(87) PCT Pub. No.: WO2021/022407
PCT Pub. Date: Feb. 11, 2021

(65) Prior Publication Data
US 2022/0249090 A1 Aug. 11, 2022

(51) Int. Cl.
*A61B 17/072* (2006.01)
*A61B 17/00* (2006.01)

(52) U.S. Cl.
CPC .. *A61B 17/072* (2013.01); *A61B 2017/00831* (2013.01); *A61B 2017/07221* (2013.01);
(Continued)

(58) Field of Classification Search
CPC ........ A61B 17/072; A61B 2017/07221; A61B 2017/07257; A61B 2017/07271; A61B 2017/07285
(Continued)

(56) References Cited

U.S. PATENT DOCUMENTS

| 1,158,111 | A | 10/1915 | Ahlheim |
| 2,891,250 | A | 6/1959 | Hirata |

(Continued)

FOREIGN PATENT DOCUMENTS

| CN | 104042288 A | 9/2014 |
| CN | 104856736 A | 8/2015 |

(Continued)

OTHER PUBLICATIONS

International Search Report (dated May 11, 2020) and Written Opinion (dated May 11, 2020), issued in corresponding International application No. PCT/CN2019/099046, 12 pages.

(Continued)

*Primary Examiner* — Valentin Neacsu
(74) *Attorney, Agent, or Firm* — Carter, DeLuca & Farrell LLP

(57) ABSTRACT

A surgical stapling device includes a tool assembly having a U-shaped frame, an anvil assembly, and a cartridge assembly. The U-shaped frame has a proximal transverse portion, a longitudinal portion, and a distal transverse portion. The distal transverse portion and the proximal transverse of the U-shaped frame and the cartridge assembly have a common shape including a first linear portion defining a first axis, a second linear portion defining a second axis, and a third linear portion defining a third axis, the first axis being transverse to the longitudinal axis of the elongate body. In embodiments, a first radius of curvature is defined between the first linear portion and the second linear portion such that (Continued)

the first axis and the second axis define an angle β, and a second radius of curvature is defined between the second linear portion and the third linear portion such that the second axis and the third axis define an angle Ω.

20 Claims, 28 Drawing Sheets

(52) U.S. Cl.
CPC ........... *A61B 2017/07257* (2013.01); *A61B 2017/07271* (2013.01); *A61B 2017/07285* (2013.01)

(58) Field of Classification Search
USPC .......................................... 227/180.1, 175.1
See application file for complete search history.

(56) References Cited

U.S. PATENT DOCUMENTS

| | | |
|---|---|---|
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et |
| 7,237,708 B1 | 7/2007 | Guy et al. |
| 7,275,674 B2 | 10/2007 | Racenet et al. |

(56) References Cited

U.S. PATENT DOCUMENTS

| | | | |
|---|---|---|---|
| RE40,237 E | 4/2008 | Bilotti et al. | |
| 7,407,076 B2 | 8/2008 | Racenet et al. | |
| 7,431,190 B2 | 10/2008 | Hoffman | |
| 7,522,854 B2 | 4/2009 | Kinouchi et al. | |
| 7,549,563 B2 | 6/2009 | Mather et al. | |
| 7,568,605 B2 | 8/2009 | Kruszynski | |
| 7,641,092 B2 | 1/2010 | Kruszynski et al. | |
| 7,717,312 B2 | 5/2010 | Beetel | |
| 7,731,073 B2 | 6/2010 | Wixey et al. | |
| 7,735,704 B2 | 6/2010 | Bilotti | |
| 7,766,207 B2 | 8/2010 | Mather et al. | |
| 7,810,690 B2 | 10/2010 | Bilotti et al. | |
| 7,886,953 B2 | 2/2011 | Schwemberger et al. | |
| 8,016,176 B2 | 9/2011 | Kasvikis et al. | |
| 8,029,520 B2 | 10/2011 | Korvick et al. | |
| 8,033,439 B2 | 10/2011 | Racenet et al. | |
| 8,070,038 B2 | 12/2011 | Kostrzewski | |
| 8,231,041 B2 | 7/2012 | Marczyk et al. | |
| 8,292,904 B2 | 10/2012 | Popovic et al. | |
| 8,360,296 B2 | 1/2013 | Zingman | |
| 8,424,738 B2 | 4/2013 | Kasvikis | |
| 8,499,994 B2 | 8/2013 | D'Arcangelo | |
| 8,596,515 B2 | 12/2013 | Okoniewski | |
| 8,627,994 B2 | 1/2014 | Zemlok et al. | |
| 8,646,673 B2 | 2/2014 | Bilotti et al. | |
| 8,757,467 B2 | 6/2014 | Racenet et al. | |
| 8,936,185 B2 | 1/2015 | Racenet et al. | |
| 8,955,732 B2 | 2/2015 | Zemlok et al. | |
| 8,967,446 B2 | 3/2015 | Beardsley et al. | |
| 9,022,273 B1 | 5/2015 | Marczyk et al. | |
| 9,125,651 B2 | 9/2015 | Mandakolathur Vasudevan et al. | |
| 9,192,382 B2 | 11/2015 | Kostrzewski | |
| 9,814,460 B2 | 11/2017 | Kimsey et al. | |
| 9,888,923 B2 | 2/2018 | Chen et al. | |
| 10,194,913 B2 | 2/2019 | Nalagatla et al. | |
| 2004/0164123 A1 | 8/2004 | Racenet et al. | |
| 2005/0247752 A1 | 11/2005 | Kelly et al. | |
| 2005/0247753 A1 | 11/2005 | Kelly et al. | |
| 2006/0163312 A1 | 7/2006 | Viola et al. | |
| 2007/0187456 A1 | 8/2007 | Viola et al. | |
| 2010/0048988 A1 | 2/2010 | Pastorelli et al. | |
| 2010/0282818 A1* | 11/2010 | Racenet | A61B 17/3209 227/181.1 |
| 2010/0282820 A1* | 11/2010 | Kasvikis | A61B 17/068 227/181.1 |
| 2013/0206813 A1 | 8/2013 | Nalagatla | |
| 2016/0249914 A1 | 9/2016 | Zhang et al. | |
| 2017/0014134 A1 | 1/2017 | Chen et al. | |
| 2017/0027571 A1 | 2/2017 | Nalagatla et al. | |
| 2017/0027572 A1 | 2/2017 | Nalagatla et al. | |
| 2017/0027573 A1 | 2/2017 | Nalagatla et al. | |
| 2017/0027574 A1 | 2/2017 | Nalagatla et al. | |
| 2017/0189021 A1 | 7/2017 | Kimsey et al. | |
| 2018/0153544 A1* | 6/2018 | Maddur Shankarsetty | A61B 90/03 |
| 2019/0000481 A1* | 1/2019 | Harris | A61B 17/07292 |
| 2022/0249090 A1* | 8/2022 | Zhang | A61B 17/072 |

FOREIGN PATENT DOCUMENTS

| | | |
|---|---|---|
| JP | 2005193042 A | 7/2005 |
| JP | 2019502464 A | 1/2019 |

OTHER PUBLICATIONS

Chinese Board Decision dated Jan. 28, 2022 with English translation, issued in corresponding CN Appln. No. 202122445206, 4 pages.
Partial Supplemental European Search Report dated Mar. 17, 2023, issued in corresponding EP Appln. No. 19940345, 20 pages.
Japanese Office Action dated Jun. 1, 2023, issued in corresponding JP Appln. No. 2022506791, 4 pages.
Extended European Search Report dated Jun. 22, 2023, issued in corresponding EP Appln. No. 19940345, 13 pages.

\* cited by examiner

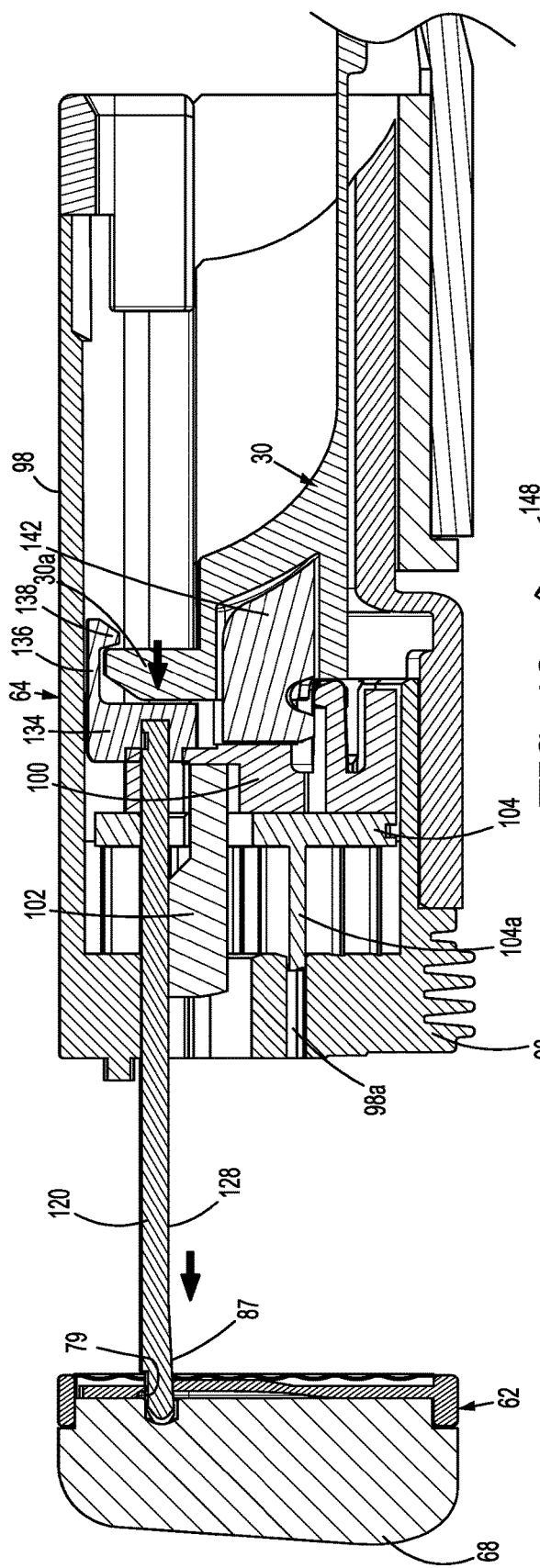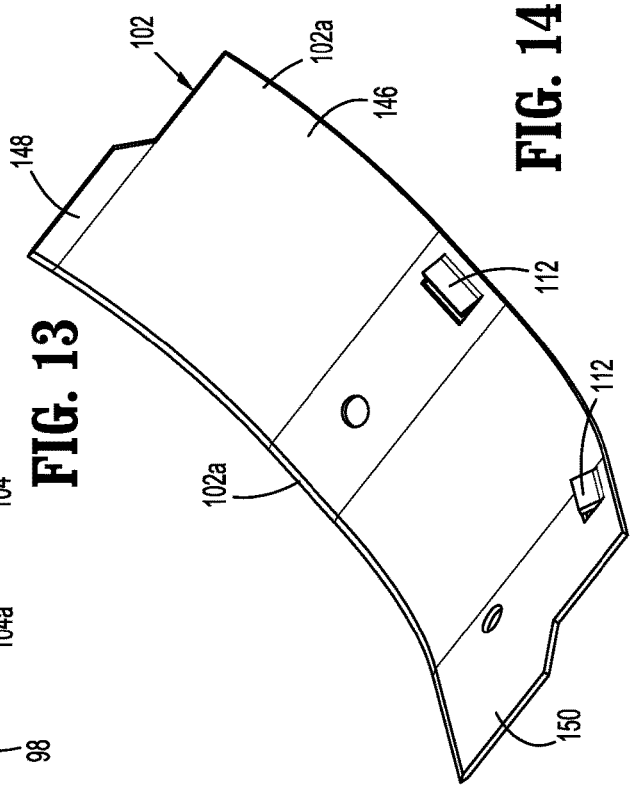

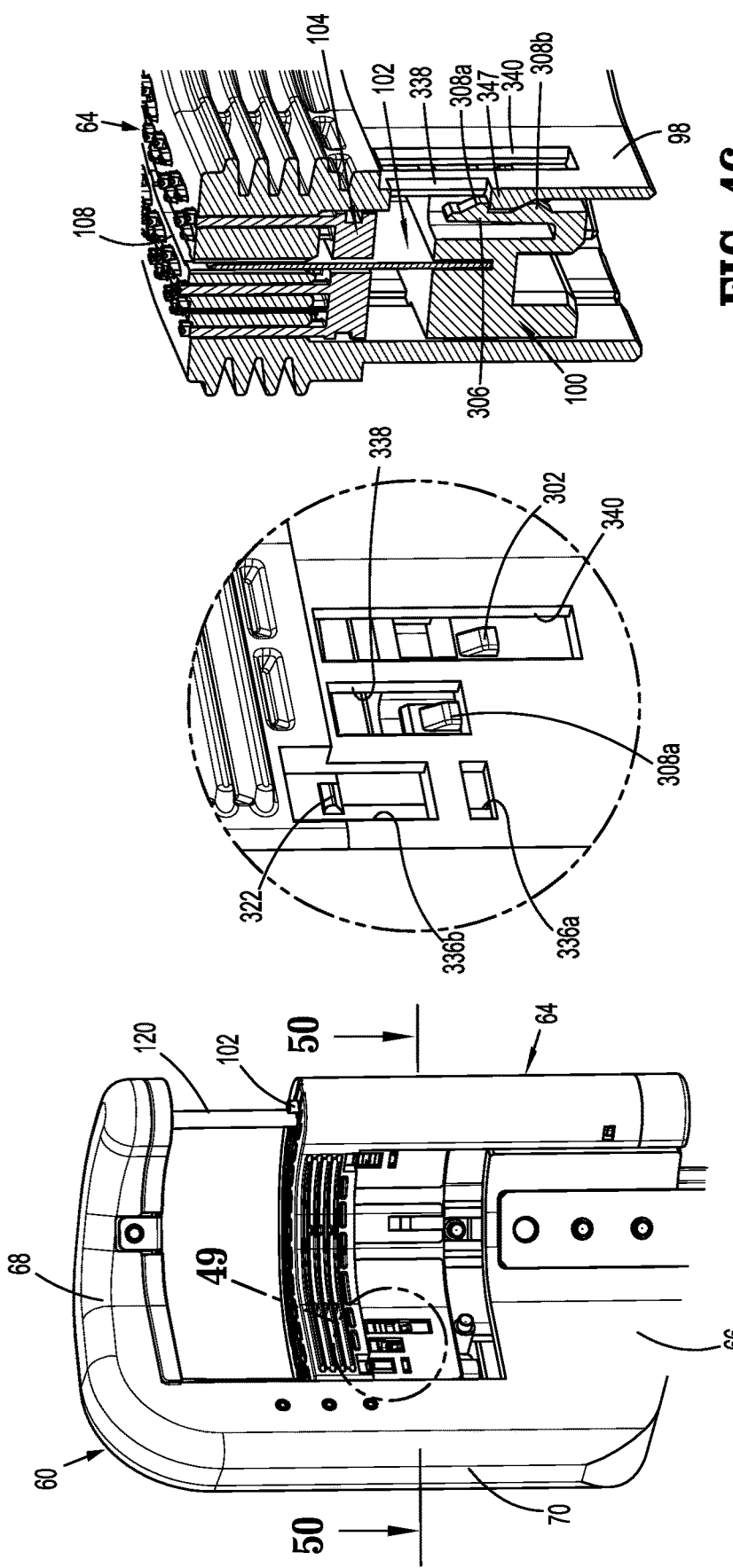

SURGICAL STAPLING DEVICE WITH CURVED TOOL ASSEMBLY

CROSS-REFERENCE TO RELATED APPLICATION

This application is a national stage of International Application No. PCT/CN2019/099046, filed Aug. 2, 2019, the entire contents of which is incorporated by reference herein.

BACKGROUND

1. Technical Description

This disclosure is directed to surgical stapling devices and, more particularly, to surgical stapling devices that include a curved tool assembly for improving access to internal body organs.

2. Background of Related Art

Surgical stapling devices are commonly used during a variety of surgical procedures to expedite dissection and suturing of tissue and minimize trauma to a patient. In certain procedures such as lower anterior resection (LAR) in which a portion of a patient's rectum or colon is removed, access to the body organ within the abdominal cavity is restricted by the human anatomy. In such procedures, the use of a surgical stapling device including a tool assembly that is specifically configured to access the internal body organ is advantageous.

A continuing need exists in the art for a surgical stapling device that is configured to improve access to certain body organs during surgical procedures.

SUMMARY

One aspect of the disclosure is directed to a surgical stapling device having an elongate body and a tool assembly. The elongate body elongate body defines a longitudinal axis and includes a proximal portion and a distal portion. The tool assembly is supported on the distal portion of the elongate body and includes an anvil assembly, a cartridge assembly, and a U-shaped frame. The U-shaped frame has a distal frame portion that extends transverse to the longitudinal axis, a proximal frame portion that extends transverse to the longitudinal axis, and a longitudinal frame portion that extends between the distal frame portion and the proximal frame portion. The anvil assembly is supported on the distal frame portion and includes an anvil plate. The cartridge assembly is supported between the proximal frame portion and the distal frame portion and is movable in relation to the anvil assembly from a retracted position in which the cartridge assembly is spaced from the anvil assembly to an advanced position in which the cartridge assembly is in juxtaposed alignment with the anvil assembly. The cartridge assembly includes a housing defining a cavity, a staple pusher positioned within the cavity, a knife holder positioned within the cavity, a knife supported on the knife holder, and an alignment pin. The knife includes side edges, and a cutting edge that extends in a direction transverse to the longitudinal axis. The alignment pin is supported within the housing of the cartridge assembly at a position spaced from the longitudinal frame portion and is movable between a retracted position recessed within the housing and an advanced position extending from the housing into engagement with the anvil assembly. The alignment pin includes a guide surface that faces the longitudinal portion of the U-shaped frame and has a distal portion that is angled towards the longitudinal portion. The knife is movable from a retracted position recessed within the housing to an advanced position extending from the housing, wherein a first side edge of the side edges of the knife is positioned to move along the guide surface of the alignment pin such that engagement of the first side edge of the knife with the distal portion of the guide surface compresses the first side edge of the knife.

In embodiments, the tool assembly includes a guide plate that is supported on the longitudinal portion of the U-shaped frame and has a guide surface that includes a distal portion that is angled inwardly away from the longitudinal portion of the U-shaped frame towards the alignment pin, wherein a second side edge of the side edges of the knife is positioned to move along the guide surface of the guide plate such that engagement of the second side edge of the knife with the distal portion of the guide surface of the guide plate compresses the second side edge of the knife.

In some embodiments, the knife has a first wing on the first side edge of the knife and a second wing on the second side edge of the knife, wherein the first wing is positioned to engage the guide surface of the alignment pin and the second wing is positioned to engage the guide surface of the guide plate.

In certain embodiments, the stapling device includes a handle assembly and the elongate body extends distally from the handle assembly.

In embodiments, the anvil assembly includes an anvil plate and a cutting plate supported on the distal frame portion of the U-shaped frame of the tool assembly. The anvil plate is positioned to receive and deform the staples and the cutting plate is positioned to engage the knife.

In some embodiments, the cutting plate is sandwiched between the distal frame portion and the anvil plate and the anvil plate defines a knife slot to facilitate passage of the knife through the anvil plate.

In certain embodiments, the cutting plate is formed from a plastic material selected from the group consisting of a polyether ether ketone (PEEK) material, a polyoxymethylene (POM) material, and a polyphenylsulfone material (PPSU).

Another aspect of the present disclosure is directed to a cartridge assembly including a housing, a pusher, a knife holder, a knife, and staples. The housing defines a cavity, a plurality of staple receiving pockets, and a knife slot, and includes an inner wall defining the cavity. The inner wall has a first ramped abutment. The staple is positioned in each of the staple receiving pockets. The pusher is movably positioned within the cavity defined by the housing from a retracted position to an advanced position and includes fingers that are received within the staple receiving slots of the housing such that movement of the pusher within the cavity from the retracted position to the advanced position urges the staples from the staple receiving slots. The knife holder is movably positioned within the cavity defined by the housing from a retracted position to an advanced position and supports the knife such that movement of the knife holder from the retracted position to the advanced position advances the knife from a position recessed within the housing to a position extending from the knife slot of the housing. The knife holder includes a body having a pair of longitudinally spaced protrusions including a distal protrusion and a proximal protrusion. In the pre-fired position of the knife holder, the distal protrusion is engaged with the first ramped abutment to obstruct advancement of the knife holder within the cavity of the housing, and in the post-fired retracted position of the knife holder, the first ramped abutment is positioned between the distal and proximal protrusions of the knife holder.

In embodiments, the housing defines a first longitudinal slot, and the distal and proximal protrusions are positioned within the first longitudinal slot when the knife holder is in its advanced position.

In some embodiments, the distal and proximal protrusions are supported on a resilient arm.

In certain embodiments, the proximal protrusion includes tapered distal and proximal surfaces and the distal protrusion includes a tapered distal face and a proximal shoulder, wherein the proximal shoulder is configured to engage the housing at a proximal end of the first longitudinal slot to obstruct further proximal movement of the knife holder within the housing.

Another aspect of the disclosure is directed to a surgical stapling device that includes an elongate body and a tool assembly. The elongate body defines a longitudinal axis and has a proximal portion and a distal portion. The tool assembly is supported on the distal portion of the elongate body and includes a U-shaped frame, an anvil assembly, and a cartridge assembly. The U-shaped frame has a proximal transverse portion, a longitudinal portion, and a distal transverse portion. The anvil assembly is supported on the distal transverse portion and the cartridge assembly is supported on the proximal transverse portion. The distal transverse portion and the proximal transverse of the U-shaped frame and the cartridge assembly have a common shape including a first linear portion defining a first axis, a second linear portion defining a second axis, and a third linear portion defining a third axis. The first axis is transverse to the longitudinal axis of the elongate body. A first radius of curvature is defined between the first linear portion and the second linear portion such that the first axis and the second axis define an angle (3, and a second radius of curvature is defined between the second linear portion and the third linear portion such that the second axis and the third axis define an angle Ω.

BRIEF DESCRIPTION OF THE DRAWINGS

Various embodiments of the disclosed surgical stapling device are described herein below with reference to the drawings, wherein:

FIG. 13 is a cross-sectional view taken along section line 13-13 of FIG. 12;

FIG. 14 is a side perspective view of the knife of the cartridge assembly of the stapling device shown in FIG. 2;

FIG. 44 is a side perspective view of the tool assembly of the stapling device shown in FIG. 1 in the fired unclamped clamped position;

FIG. 45 is an enlarged view of the indicated area of detail shown in FIG. 44;

FIG. 46 is a side cross-sectional view taken through a first portion of the cartridge assembly with the cartridge assembly in a fired unclamped position;

DETAILED DESCRIPTION OF EMBODIMENTS

Figure 1:
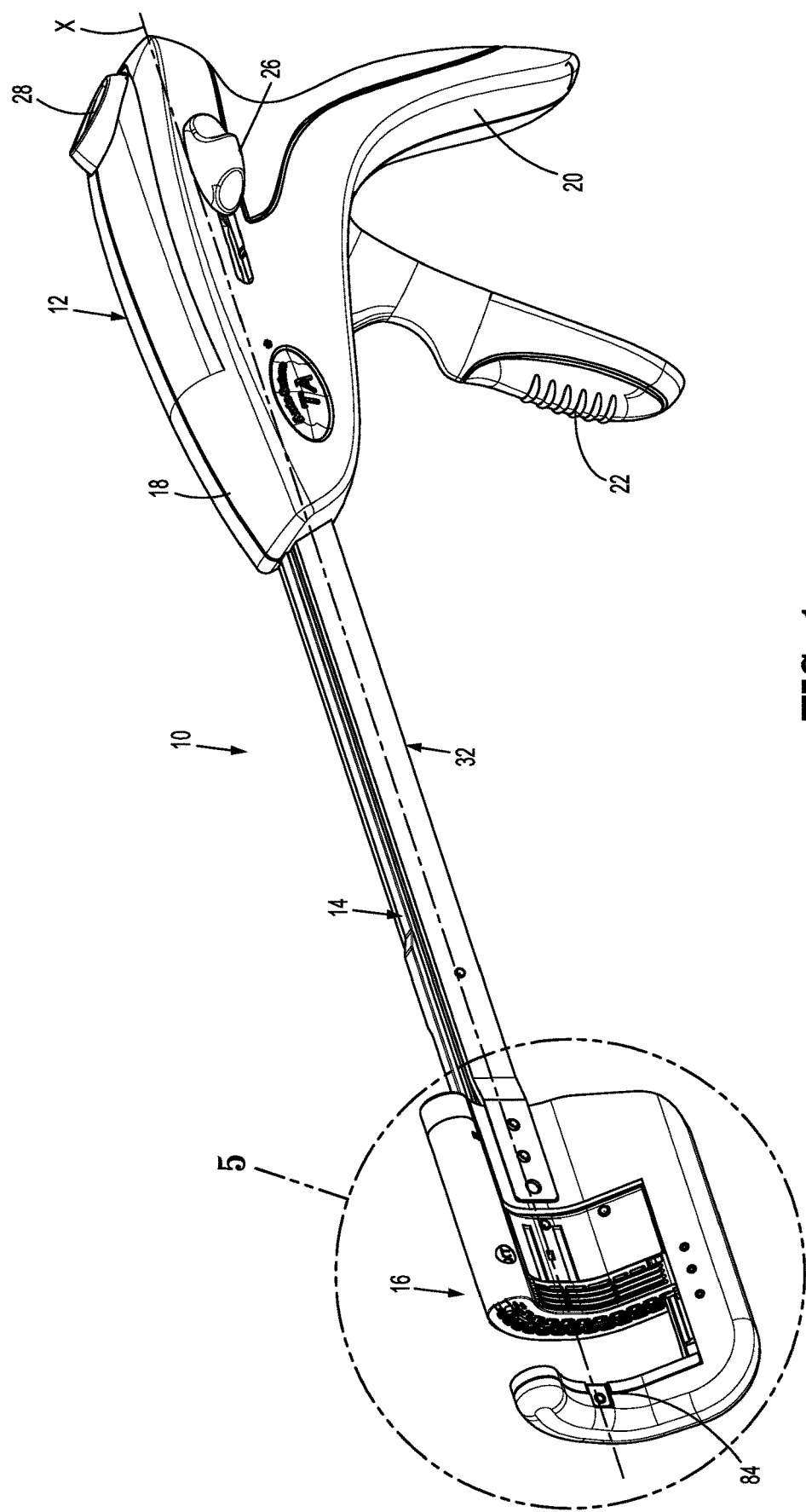
FIG. 1 is a side perspective view of an exemplary embodiment of the disclosed stapling device with a tool assembly in an unclamped position and an alignment pin in a retracted position.

The disclosed surgical stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the terms "about" and "substantially" are used to refer to between 90 to 110 percent of the identified parameter. Further, the term "clinician" is used generally to refer to medical personnel including doctors, nurses, and support personnel.

Figure 2:
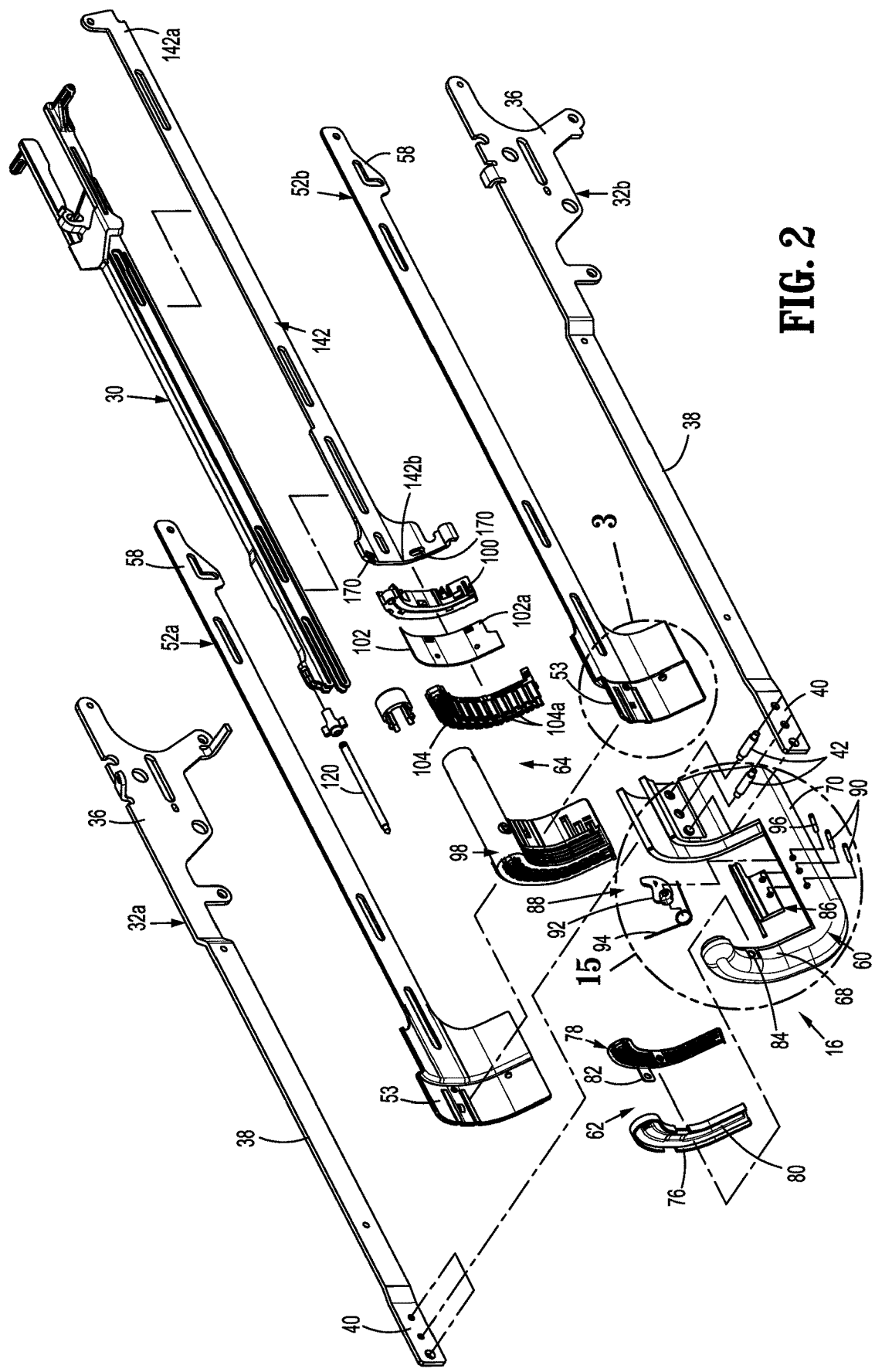
FIG. 2 is an exploded view of an elongate body and the tool assembly of the stapling device shown in FIG. 1.
Figure 3:
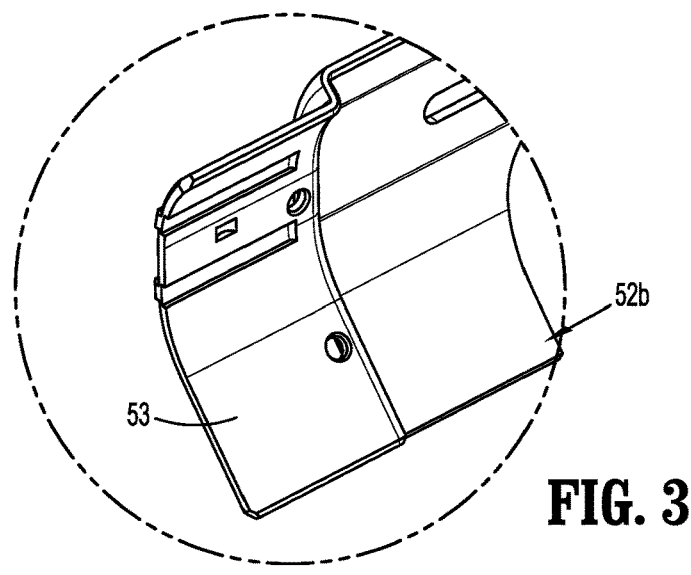
FIG. 3 is an enlarged view of the indicated area of detail shown in FIG. 2.
Figure 4:
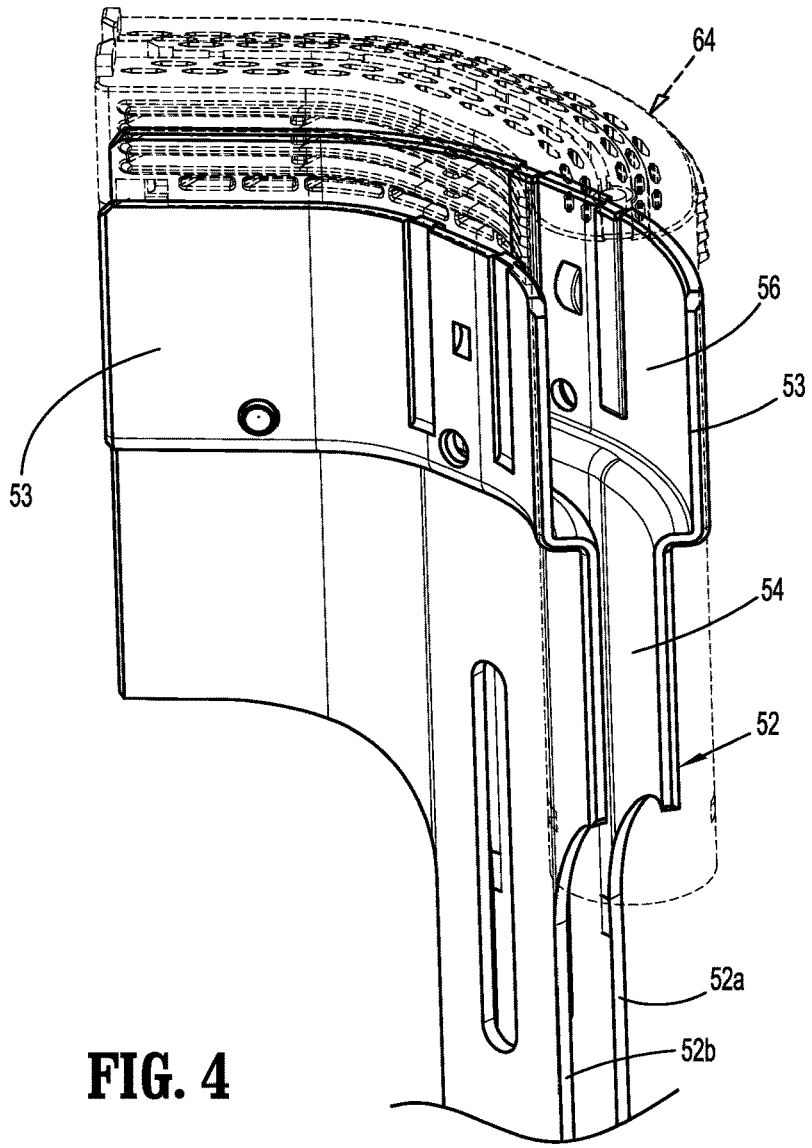
FIG. 4 is a side perspective view of a clamp slide assembly of the stapling device shown in FIG. 2 illustrating the cartridge assembly in phantom.
Figure 6:
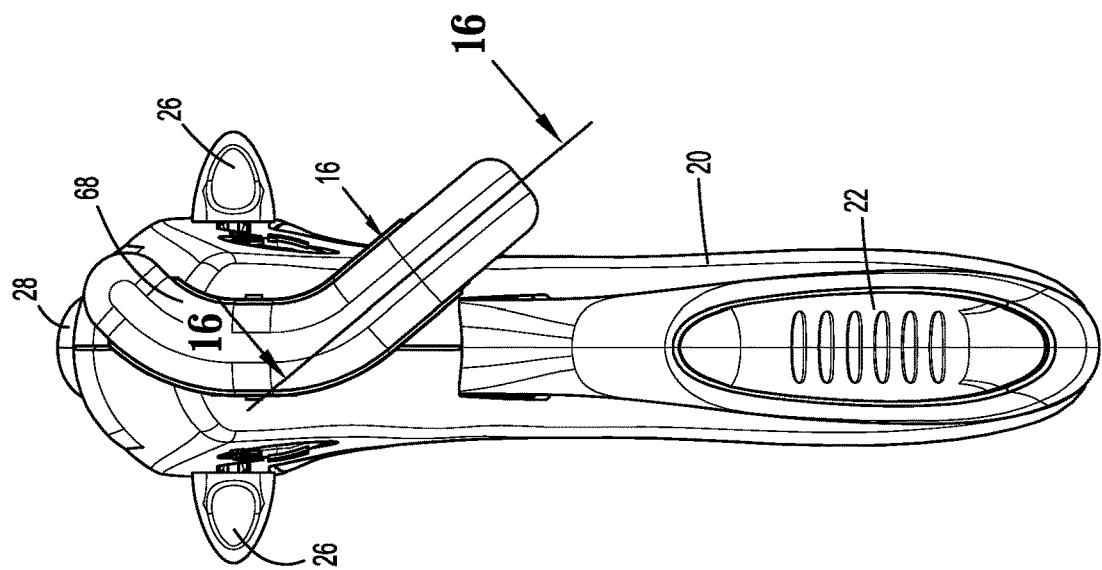
FIG. 6 is a perspective view from the distal end of the stapling device shown in FIG. 1.

The disclosed surgical stapling device is shown generally in FIG. 1 as stapling device 10 and includes a handle assembly 12, an elongate body 14 that extends distally from the handle assembly 12, and a tool assembly 16 that is supported on a distal portion of the elongate body 14. The elongate body 14 defines a longitudinal axis "X". The handle assembly 12 includes a housing 18 that defines a stationary handle 20 and supports a movable trigger 22. In embodiments, the movable trigger 22 is supported by the housing 18 to pivot towards the stationary handle 20 between non-actuated and actuated positions to operate the tool assembly 16. The handle assembly 12 also supports buttons 26 that are supported on each side of the housing 18 and are movable along the housing 18 to advance and retract an alignment pin pusher 30 (FIG. 2). The handle assembly 12 also includes a release button 28 that can be depressed to move the tool assembly 16 from a clamped position to an unclamped position. For a more detailed description of a suitable handle assembly 12, see U.S. Pat. No. 6,817,508 ("the '508 Patent") which is incorporated herein in its entirety by reference.

Referring to FIG. 2, the stapling device 10 includes a frame assembly 32 (FIG. 1) including a first frame member 32a and a second frame member 32b. The frame members 32a, 32b are formed of a rigid material such as stainless steel and include proximal portions 36 that form part of the handle assembly 12 and distal elongate portions 38 that form part of the elongate body 14. A distal end portion 40 of each of the distal elongate portions 38 of the frame assembly 32 is adapted to be coupled to the tool assembly 16 such that the tool assembly 16 is supported on the distal end portion 40 of the elongate body 14. In embodiments, rivets 42 are used to connect the ends of the frame members 32a, 32b together such that the frame members 32a, 32b are secured to each other in spaced relation to define a longitudinal slot 44 (FIG. 5) that receives various components of the stapling device 10 including the alignment pin pusher 30 as described in further detail below.

Referring to FIGS. 2-5, the stapling device 10 includes a clamp slide assembly 52 (FIG. 4) that includes a first clamp slide member 52a and a second clamp slide member 52b. The clamp slide members 52a and 52b are secured together in spaced relation to each other using rivets or the like to define a longitudinal recess 54. The clamp slide members 52a and 52b have distal end portions 53 that are stepped outwardly such that a distal portion of the longitudinal recess 54 of the clamp slide assembly 52 defines a cartridge receiving cavity 56 (FIG. 4) that has a width that is greater than the width of a proximal portion of the longitudinal recess 54.

The clamp slide assembly 52 is received within the longitudinal slot 44 (FIG. 5) defined by the frame members 32a, 32b. Each of the clamp slide members 52a, 52b includes a proximal end portion 58 that is coupled to the handle assembly 12 such that movement of the movable trigger 22 (FIG. 1) between the non-actuated and actuated positions causes longitudinal movement of the clamp slide assembly 52 within the longitudinal slot 44 (FIG. 5) defined by the frame assembly 32. For a more detailed description of the interaction between the handle assembly 12 and the clamp slide assembly 52, see the '508 Patent.

Referring also to FIGS. 5-7, and 15, the tool assembly 16 includes a substantially U-shaped frame 60, an anvil assembly 62, and a cartridge assembly 64. The frame 60 includes a proximal transverse portion 66, a distal transverse portion 68, and a longitudinal portion 70 interconnecting the proximal transverse portion 66 and the distal transverse portion 68. The proximal and distal transverse portions 66 and 68, respectively, are curved along an axis (FIG. 6) that is transverse to the longitudinal axis "X" (FIG. 1). More specifically, the proximal and distal transverse portions 66 and 68, respectively, have shapes that correspond to each other and to the shape of the cartridge assembly 64 and include a first linear portion 69a (FIG. 6A), a second linear portion 69b, and a third linear portion 69c. As illustrated in FIG. 6A, the first linear portion 69a extends along an axis L that is substantially transverse to the longitudinal axis X of the stapling device 10, the second linear portion 69b extends along an axis M that defines an angle β in relation to the first linear portion 69a, and the third linear portion 69c extends along an axis N that defines an angle 1 in relation to the second linear portion 69b. A first radius of curvature is defined between the first linear portion 69a and the second linear portion 69b and a second radius of curvature is defined between the second linear portion 69b and the third linear portion 69c. In embodiments, angle β is from about 92 degrees to about 178 degrees, and angle Ω is from about 92 degrees to about 178 degrees. In some embodiments, angle θ is about 120 degrees and angle Ω is about 120 degrees. The disclosed configuration of the tool assembly 16 provides greater access to the pelvic structure of the human body.

Figure 5:
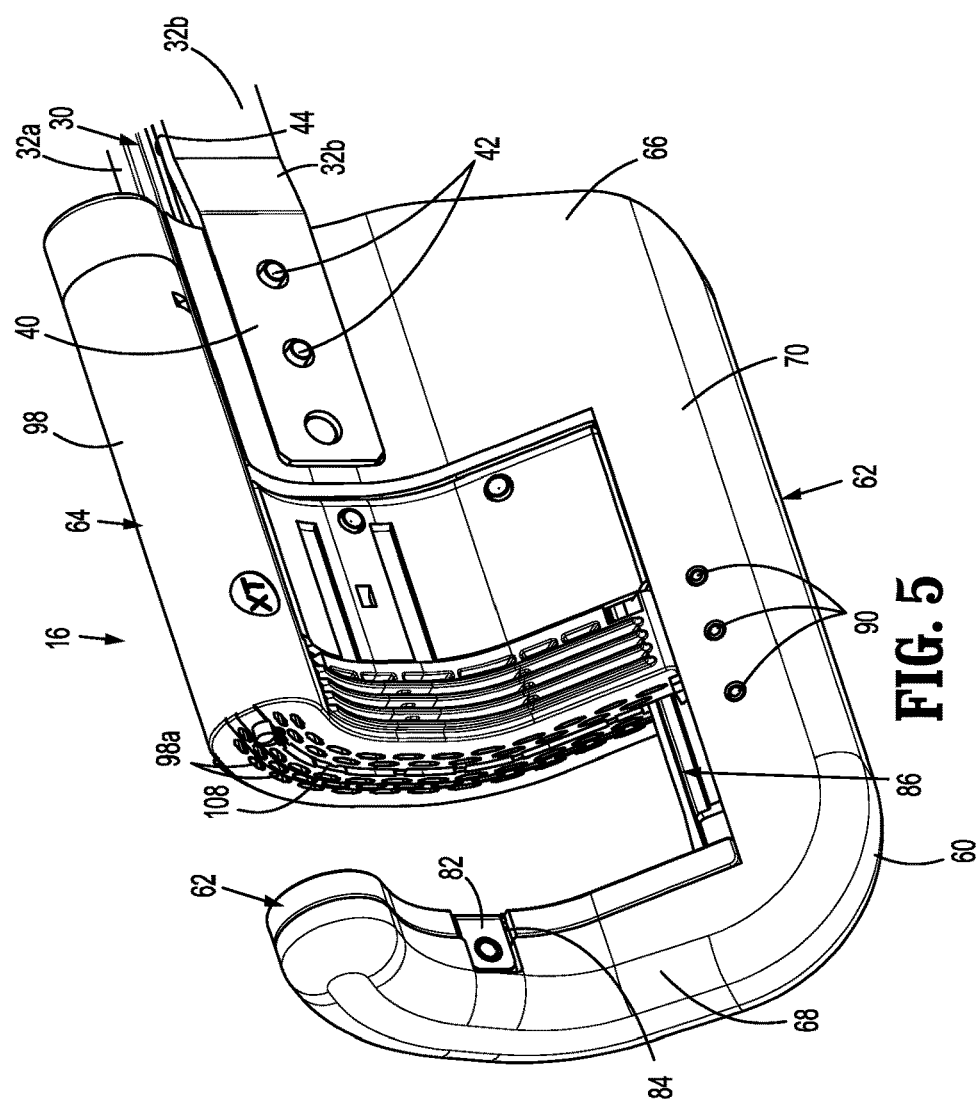
FIG. 5 is an enlarged view of the indicated area of detail shown in FIG. 1.
Figure 6A:
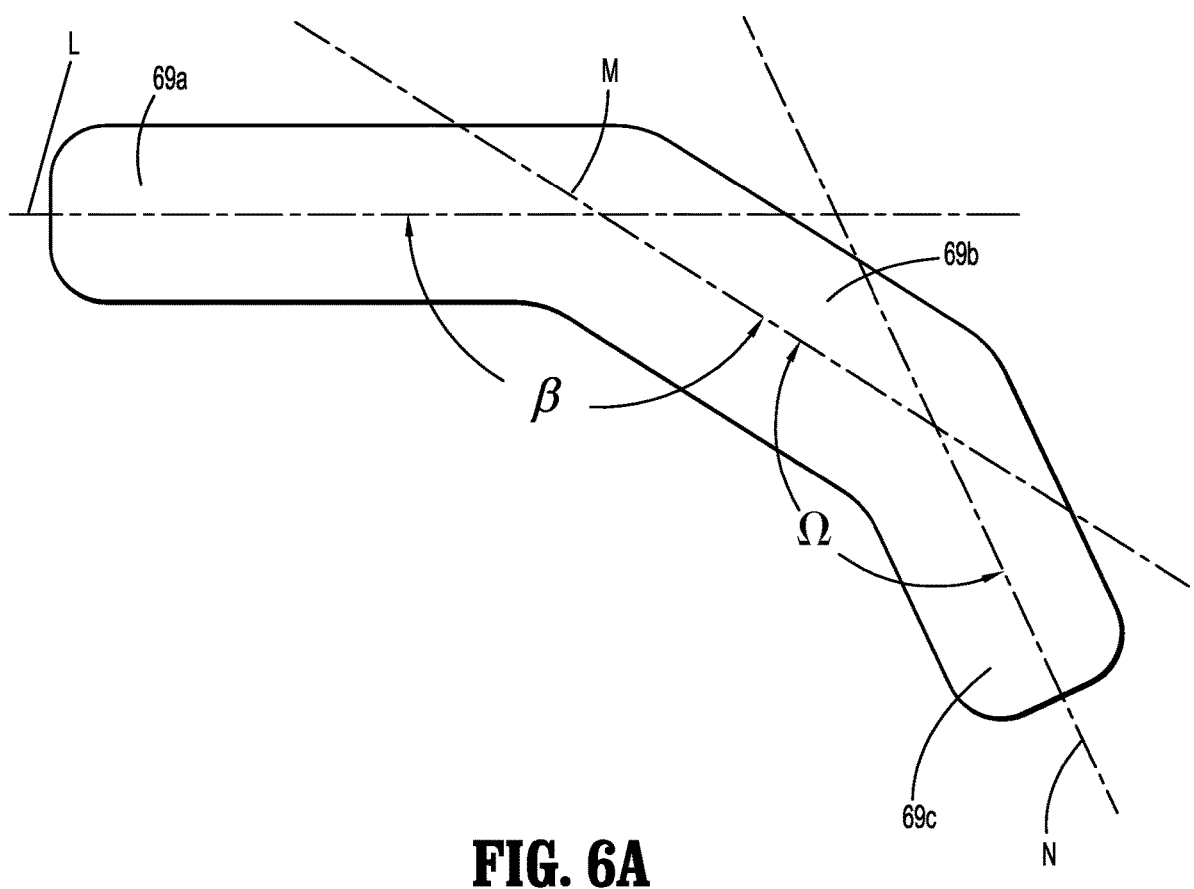
FIG. 6A is a front view of the tool assembly of the stapling device shown in FIG. 1.
Figure 7:
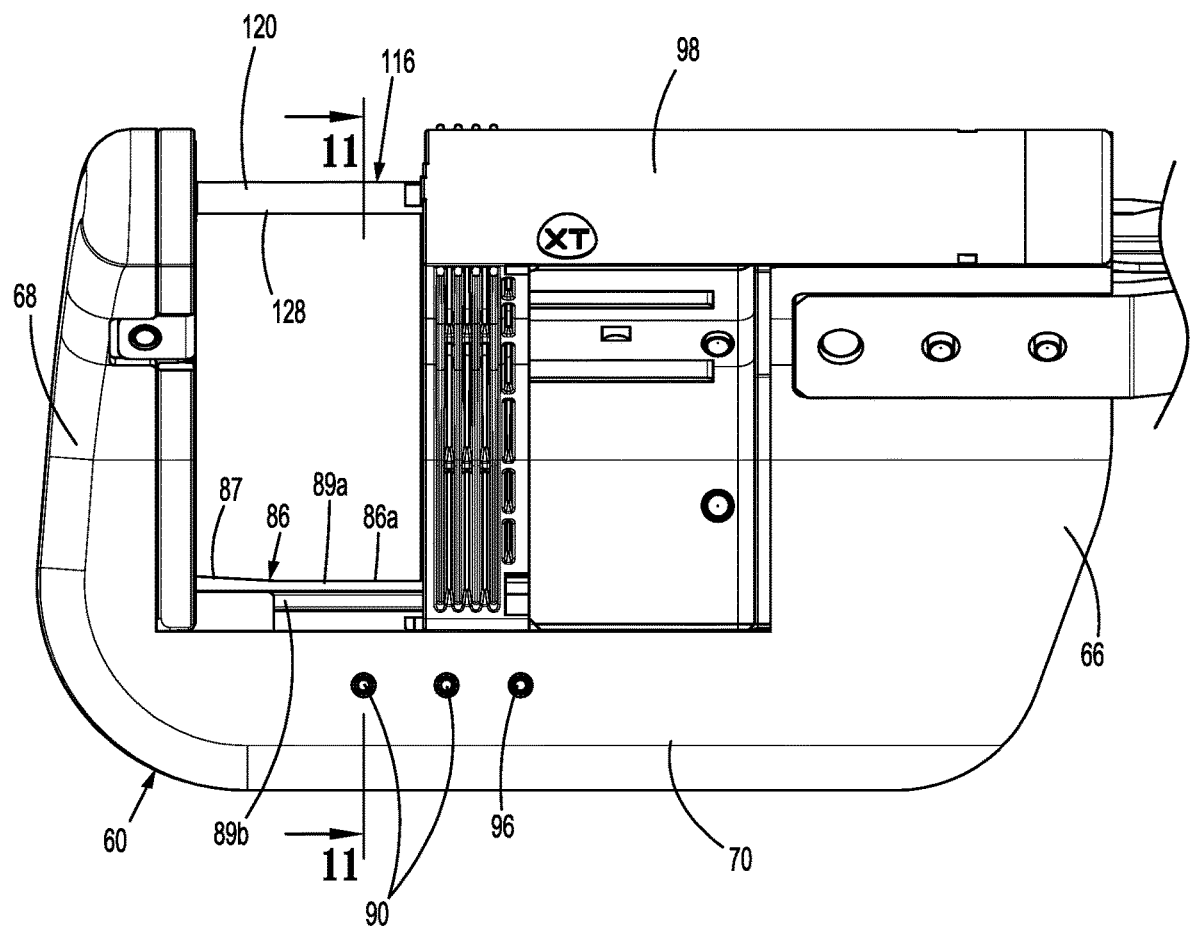
FIG. 7 is a side view of the tool assembly of the stapling device shown in FIG. 1 with the tool assembly in the unclamped position and the alignment pin in an advanced position.
Figure 8:
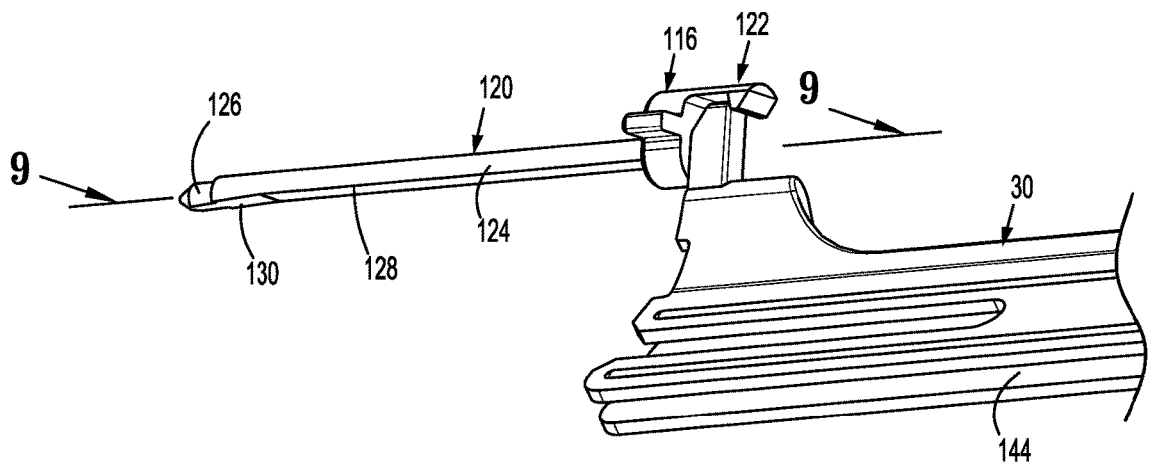
FIG. 8 is a side perspective view of the distal end of an alignment pin pusher and the alignment pin of the stapling device shown in FIG. 2.
Figure 9:
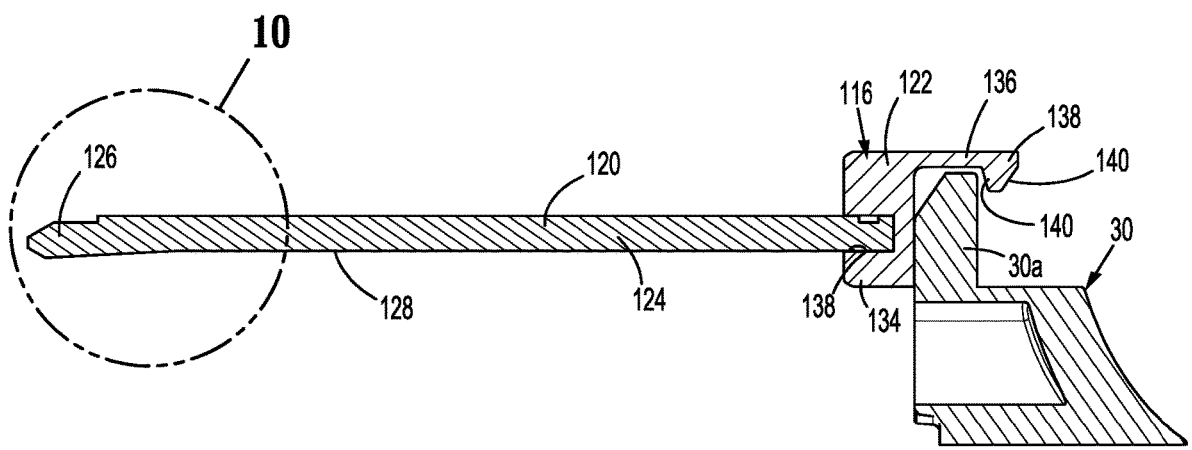
FIG. 9 is a cross-sectional view taken along section line 9-9 of FIG. 8.
Figure 10:
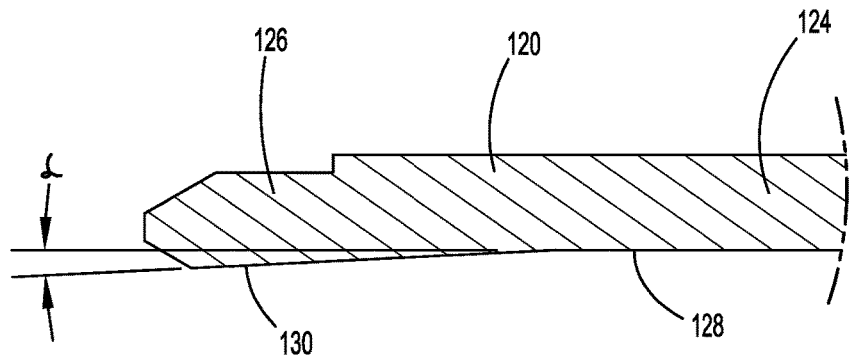
FIG. 10 is an enlarged view of the indicated area of detail shown in FIG. 9.
Figure 12:
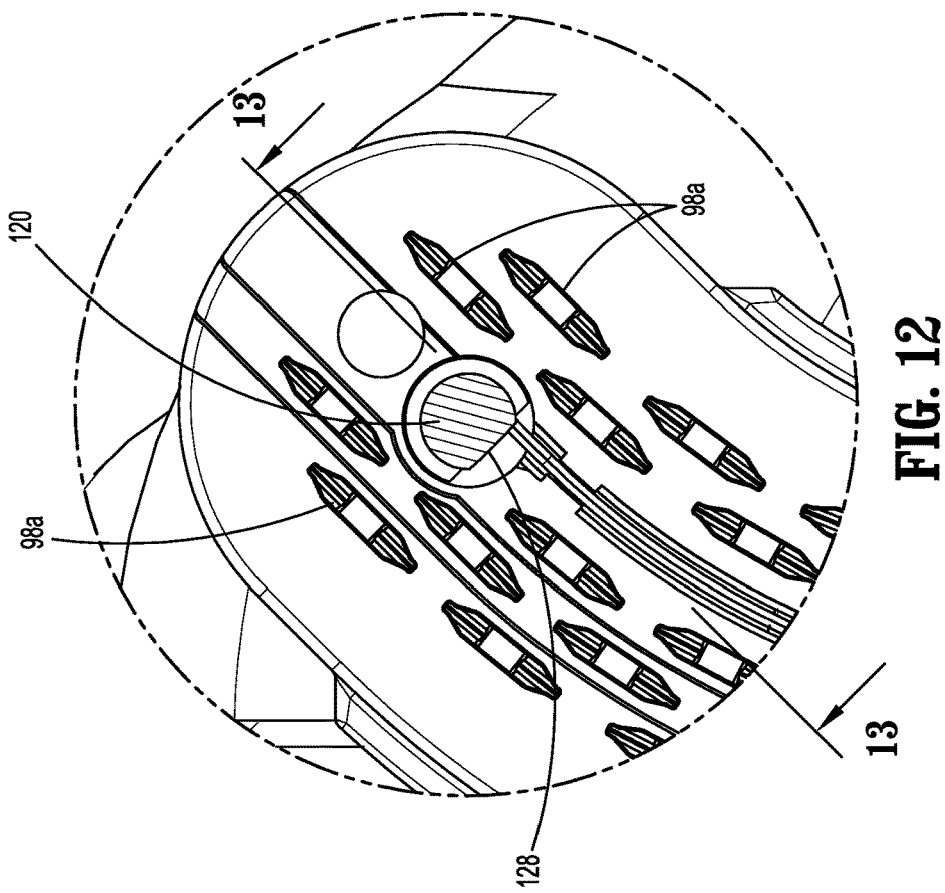
FIG. 12 is an enlarged view of the indicated area of detail shown in FIG. 11.
Figure 11:
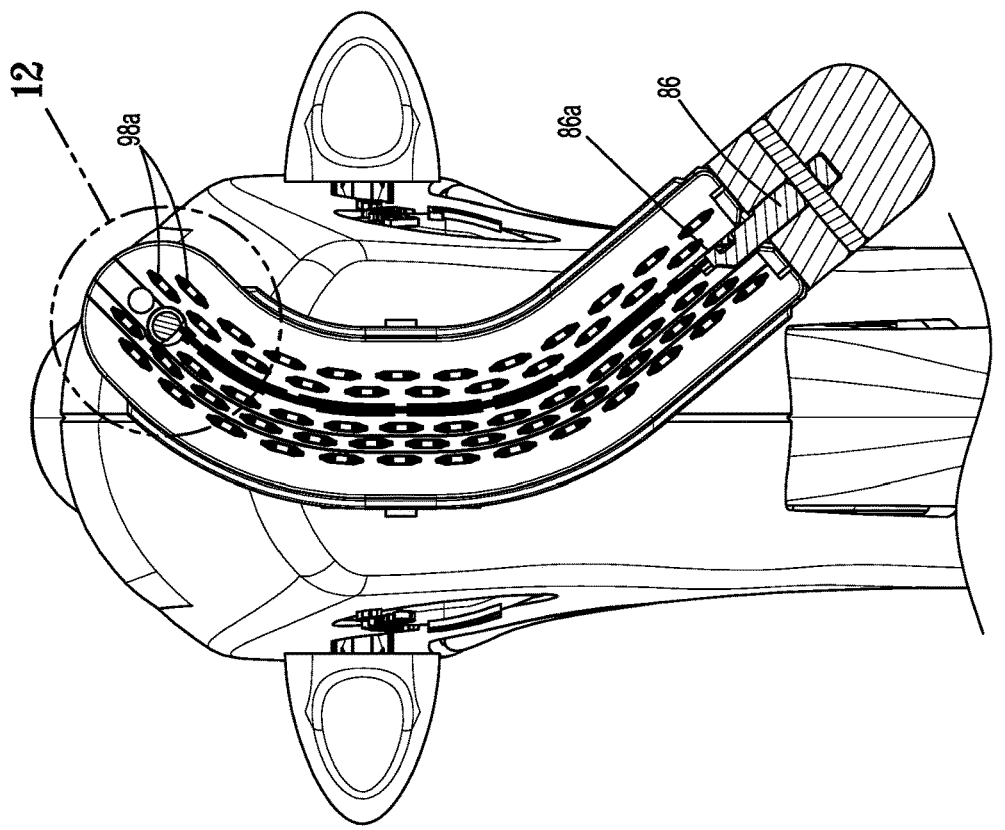
FIG. 11 is a cross-sectional view taken along section line 11-11 of FIG. 7.

The distal transverse portion 68 of the frame 60 of the tool assembly 16 supports the anvil assembly 62 (FIG. 5). In embodiments, the anvil assembly 62 includes a cutting plate 76 and an anvil plate 78 (FIG. 2). The anvil plate 78 defines a knife slot 78a. The cutting plate 76 and the anvil plate 78 define alignment pin bores 79 (FIG. 13) that receive an alignment pin 120 as described in further detail below. The cutting plate 76 (FIG. 2) and the anvil plate 78 have shapes that correspond to the shape of the distal transverse portion 68 of the frame 60. The cutting plate 76 defines a distal cavity 80 (FIG. 2) that receives the distal transverse portion 68 of the frame 60 such that the cutting plate 76 is received and supported on the distal transverse portion 68 of the frame 60. The anvil plate 78 is positioned on top of the cutting plate 76 such that the cutting plate 76 is sandwiched between the anvil plate 78 and the distal transverse portion 68 of the frame 60. In embodiments, the anvil plate 78 includes flanges 82 (FIG. 2) and the distal transverse portion 68 of the frame 60 and the cutting plate 76 define cutouts 84 and 84a. The flanges 82 are secured within the cutouts 84 and 84a to secure the anvil assembly 62 to the distal transverse portion 68 of the frame 60.

The tool assembly 16 also includes a guide plate 86 and a lockout assembly 88 (FIG. 2). The guide plate 86 (FIG. 7) is positioned on the longitudinal portion 70 of the frame 60 of the tool assembly 16 between the distal transverse portion 68 and the proximal transverse portion 66. In embodiments, the guide plate 86 is secured to the longitudinal portion 70 of the frame 60 using rivets 90, screws, or the like and includes a guide surface 86a that faces away from the longitudinal portion 70 of the U-shaped frame 60. The guide surface 86a may be substantially flat although other configurations are envisioned.

Figure 15:
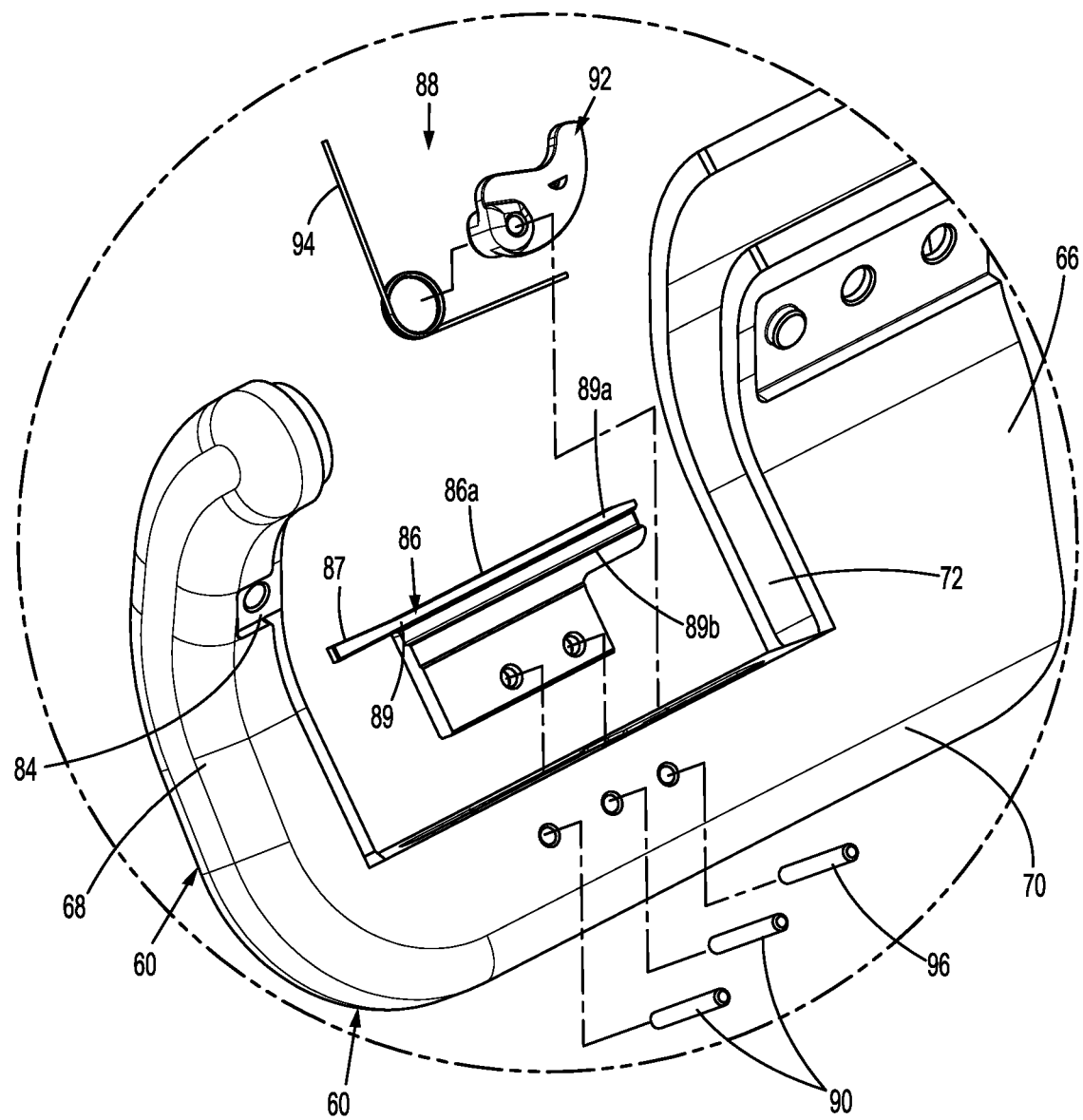
FIG. 15 is an enlarged view of the indicated area of detail shown in FIG. 2.

A distal portion 87 of the guide surface 86a is angled inwardly away from the longitudinal portion 70 of the frame 60 of the tool assembly 16. In embodiments, the guide plate 86 includes a head portion 89a and a base portion 89b (FIG. 15). The head portion 89a defines a T-shape with the base portion 89b and is received in a lower portion of the cartridge assembly 64 to guide movement of the cartridge assembly 64 between retracted and advanced positions.

Figure 27:
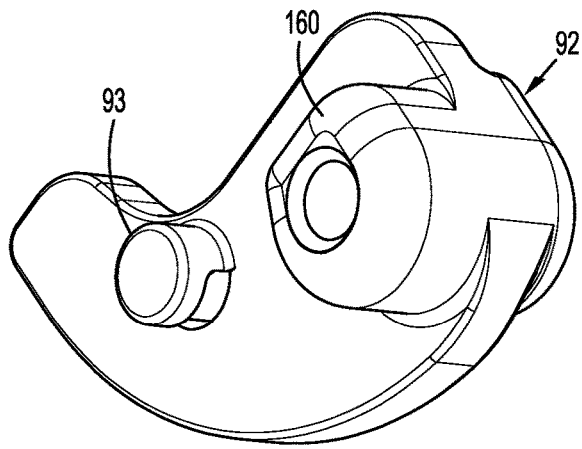
FIG. 27 is a side perspective view of a lockout member of the stapling device shown in FIG. 2.

FIG. 15 illustrates the lockout assembly 88 which includes a lockout member 92 and a biasing member 94. The lockout member 92 includes a biasing member mount 93 (FIG. 27). In embodiments, the lockout member 92 is rotatably mounted about a pivot member 96 to the longitudinal portion 70 of the U-shaped frame 68 of the tool assembly 16. The lockout member 92 can pivot between a locked position (FIG. 28) and an unlocked position. In embodiments, the biasing member 94 (FIG. 15) includes a torsion spring that has a first end engaged with the biasing member mount 93 and is positioned within the U-Shaped frame 60 of the tool assembly 16 to urge the lockout member 92 to the locked position as described in detail below.

Figure 16:
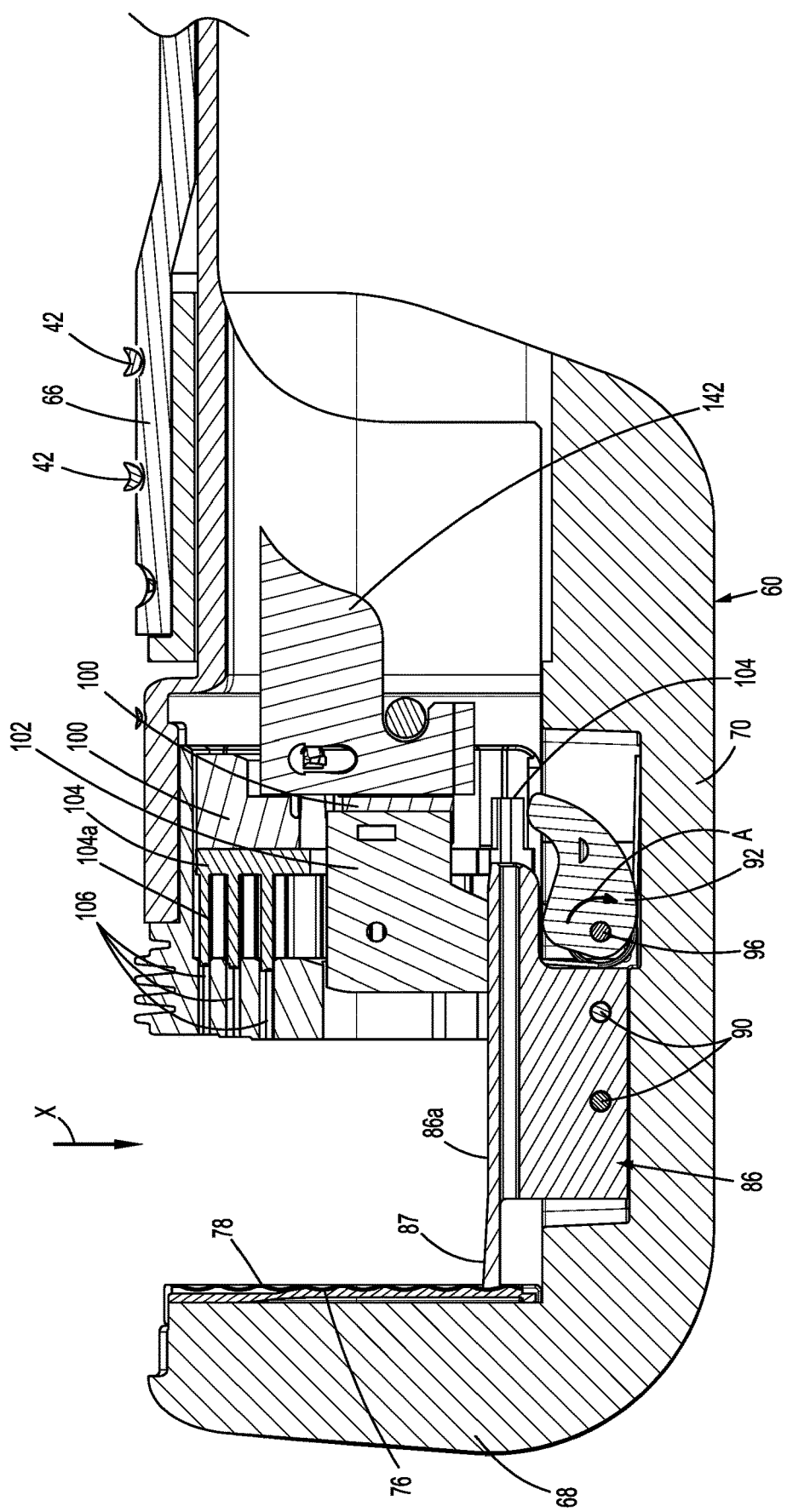
FIG. 16 is a cross-sectional view taken along section line 16-16 of FIG. 6.

FIGS. 2-5 illustrate the cartridge assembly 64 which includes a housing 98, a knife holder 100, a knife 102 having a cutting edge 102a (FIG. 14), a pusher 104, and a plurality of staples 106 (FIG. 16). The housing 98 defines a cavity, a plurality of staple receiving pockets 98a (FIG. 5), and a knife slot 108. Each of the staple receiving pockets 98a receives a staple 106 (FIG. 16).

The pusher 104 is positioned within the cavity of the housing 98 and includes fingers 104a that are received within the staple receiving pockets 98a when the pusher 104 is moved from a retracted position to an advanced position within the housing 98 to eject staples 106 from the cartridge assembly 64. The knife holder 100 supports the knife 102 and is movable within the housing 98 of the cartridge assembly 64 such that the knife 102 is movable through the knife slot 108 (FIG. 5) in the housing 98 during firing of the stapling device 10 as described in further detail below.

In embodiments, the knife 102 includes a proximal portion 102a that is received in a recess 110 (FIG. 32) defined in the knife holder 100 to secure the knife 102 to the knife holder 100. The knife 102 may include tabs 112 (FIG. 14) to facilitate securement of the knife 102 within the recess 110 of the knife holder 100. In some embodiments, the plurality of staple receiving pockets 98a are aligned in rows and the knife slot 108 (FIG. 32) is positioned between the rows of staples. In certain embodiments, two or more rows of staples are positioned on each side of the knife slot 108 (FIG. 5). The knife holder 100 and the pusher 104 are movable within the housing 98 of the cartridge assembly 64 from a retracted position to an advanced position to eject the staples 106 from the housing 98 and to advance the knife 102 through the knife slot 108 as described in further detail below.

Referring to FIGS. 2 and 7-13, the cartridge assembly 64 also includes an alignment pin assembly 116 that is supported in the housing 98 of the cartridge assembly 64 at a position spaced from the longitudinal portion 70 of the frame 60 and the guide plate 86. The alignment pin assembly 116 includes an alignment pin 120 and an alignment pin coupling member 122. The alignment pin 120 includes a substantially D-shaped body 124 having a distal head portion 126 of reduced diameter, and a guide surface 128 that faces the longitudinal portion 70 of the frame 60 of the tool assembly 16 when the cartridge assembly 64 is received within the cartridge receiving cavity 56 (FIG. 4) of the clamp slide assembly 52. In embodiments, the guide surface 128 is substantially flat and includes a distal portion 130 that is angled towards the longitudinal portion 70 of the frame 60 in a distal direction. In some embodiments, the distal portion 130 of the flat surface 128 defines an angle £ (FIG. 10) with a longitudinal axis of the alignment pin 120, wherein £ is from about 2 degrees to about 10 degrees.

The coupling member 122 is secured to a proximal end of the alignment pin 120 and includes a base 134 and a proximally extending resilient finger 136. In embodiments, the base 134 defines a bore 138 (FIG. 9) that receives the proximal end of the alignment pin 120 to secure the alignment pin 120 to the base 134 and the finger 136 includes a downwardly extending protrusion 138. The downwardly extending protrusion 138 includes angled distal and proximal surfaces 140 and is configured to engage or be coupled to a distal end portion of the alignment pin pusher 30. More specifically, the distal end portion of the alignment pin pusher 30 includes a finger 30a that is positioned to be received within the housing 98 of the cartridge assembly 64 between the protrusion 138 of the resilient finger 136 and the base 134 of the coupling member 134 when the cartridge assembly 64 is received within the cartridge receiving cavity 56 of the clamp slide assembly (FIG. 4) to couple the alignment pin pusher 30 to the alignment pin 120.

The stapling device 10 further includes a thrust bar 142 that is shown in FIG. 2 and has a proximal portion 142a (FIG. 2) that is received within the handle assembly 12 (FIG. 1) and a distal portion 142b that is movable into engagement with the knife holder 100. The thrust bar 142 has a distal end portion 142b that is configured to engage the knife holder 100 as described in further detail below to couple the thrust bar 142 to the knife holder 100.

The alignment pin pusher 30 defines an elongate slot 144 (FIG. 8) that receives the thrust bar 142. The elongate slot 144 is configured and dimensioned to facilitate longitudinal movement of the alignment pin pusher 30 independently of the thrust bar 142 to allow a clinician to advance the alignment pin 120 prior to actuation of the thrust bar 142. As described in detail in the '508 Patent, the alignment pin pusher 30 can be manually or automatically advanced to advance the alignment pin 120 into engagement with the anvil assembly 62. When the alignment pusher 30 is manually advanced, the alignment pin pusher 30 moves independently of the thrust bar 142. In the advanced position of the alignment pin pusher 30, the distal head portion 126 of the alignment pin 120 extends through the alignment pin bores 79 (FIG. 14) in the cutting plate 76 and anvil plate 78 of the anvil assembly 62 to confine tissue within the tool assembly 16 between the alignment pin 120 and the guide plate 86, and to provide stability to the tool assembly 16 during operation of the stapling device 10. In embodiments, the distal head portion 126 and the alignment pin bores 79 are dimensioned to have an interference fit.

Referring to FIGS. 11-19, when a cartridge assembly 64 is inserted into the cartridge receiving cavity 56 defined by the distal portion of the clamp slide assembly 52 and the clamp slide assembly 52 is moved from a retracted position to an advanced position via actuation of the movable trigger 22 (FIG. 1), the cartridge assembly 64 is moved in relation to the anvil assembly 62 from the unclamped position to the clamped position to position the cartridge assembly 64 in juxtaposed alignment with the anvil assembly 62. This operation is described in detail in the '508 Patent. When the thrust bar 142 is coupled to the knife holder 100, advancement of the thrust bar 142 causes corresponding advancement of the knife holder 100 and of the knife 102 within the cartridge housing 98 towards the anvil assembly 62.

The knife 102 includes a body 146 (FIG. 14) having wings 148, 150. The wing 148 is positioned to ride along the guide surface 86a of the guide plate 86 (FIG. 19) and the wing 150 is positioned to ride along the guide surface 128 (FIG. 17) of the alignment pin 120. In embodiments, engagement between the wings 148 and 150 of the knife 102 and the guide plate 86 and the guide surface 128 of the alignment, respectively, causes deformation of the wings 148 and 150. As discussed above, the guide surface 86a of the guide plate 86 includes a distal portion 87 (FIG. 19) that is angled inwardly away from the longitudinal portion 70 of the frame 60 towards the alignment pin 120. Similarly, the guide surface 128 of the alignment pin 120 includes a distal portion 130 that is angled towards the longitudinal portion 70 of the frame 60 and the guide plate 86. The angled portions of the guide surfaces 86, 128 of the guide plate 86 and the alignment pin 120 ensures that no gap exists between the knife 102 and alignment pin 120 and the knife 102 and the guide plate 86. This ensures that tissue confined within the tool assembly 16 is fully dissected by the knife 102.

Figure 20:
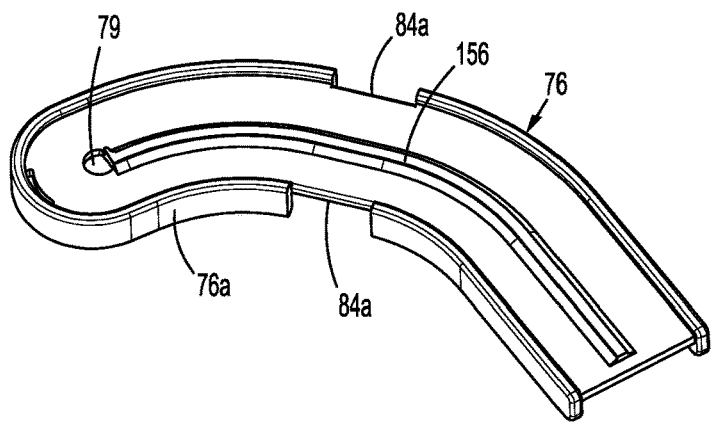
FIG. 20 is a perspective view from the proximal end of a cutting plate of an anvil assembly of the tool assembly shown in FIG. 17.
Figure 22:
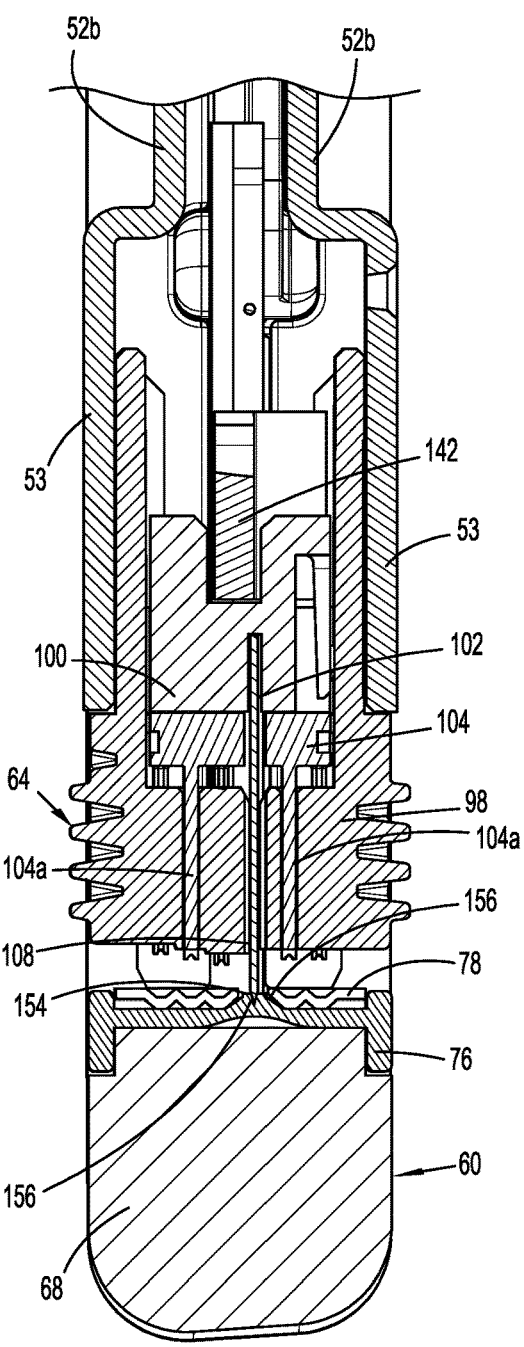
FIG. 22 is a cross-sectional view taken along section line 22-22 of FIG. 17.
Figure 21:
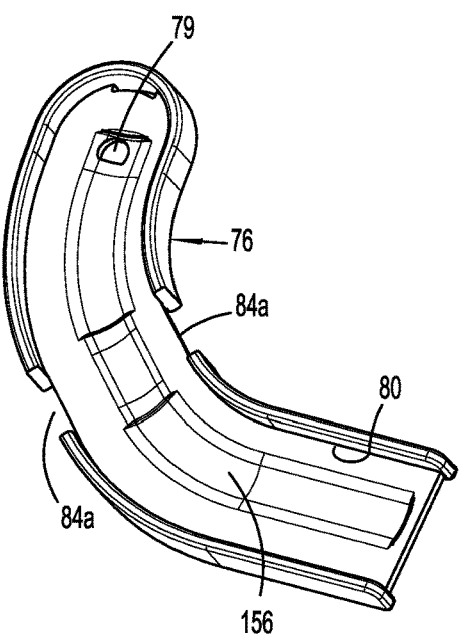
FIG. 21 is a perspective view from the distal end of the cutting plate shown in FIG. 20.

Referring to FIGS. 20-22, the anvil plate 78 (FIG. 22) defines a curved knife slot 154 that is aligned with the curved knife slot 108 in the housing 98 of the cartridge assembly 64 when the cartridge assembly 64 is in the clamped position. In embodiments, the cutting plate 76 is positioned to receive the cutting edge 102a (FIG. 14) of the knife 102 after the knife 102 passes through the curved knife slot 154 in the anvil plate 78. The cutting plate 76 may include a body 76a having a curved ridge 156 that is aligned with the knife slot 154 in the anvil plate 78. Similarly, the cutting plate 76 may include a concavity on an opposite side of the cutting plate 76 opposite to the curved ridge 156 within the distal cavity 80 of the cutting plate 76. In embodiments, the cutting plate 76 is formed from a plastic material such as a polyether ether ketone (PEEK) material, a polyoxymethylene (POM) material, or a polyphenylsulfone material (PPSU). In some embodiments, the cutting plate 76 is formed by injection molding although other methods of manufacture are envisioned. The cutting plate 76 should be formed of a material that will deform locally and structurally upon engagement with the knife 102. Local deformation of the cutting plate 76 ensures that no gap exists between the knife 102 and the surface of the cutting plate 76 to facilitate a clean cut through tissue. The structural deformation limits the firing force required to fire the stapling device 10.

Figure 18:
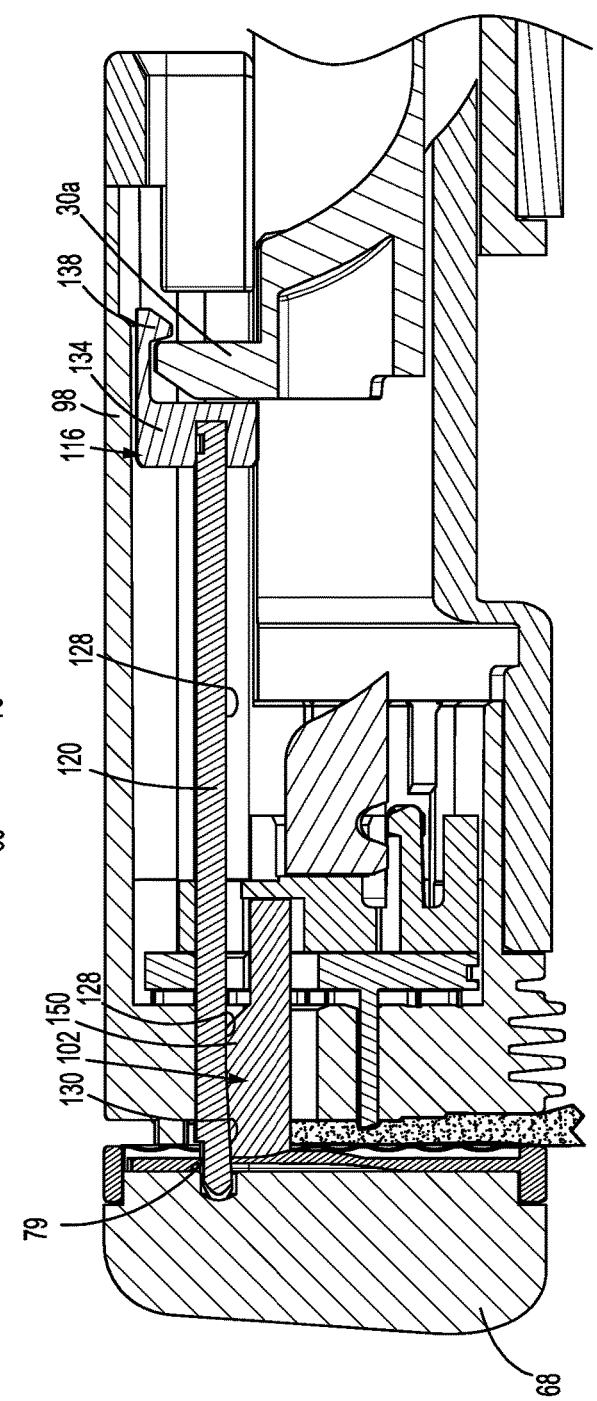
FIG. 18 is a cross-sectional view taken along section line 18-18 of FIG. 17.
Figure 19:
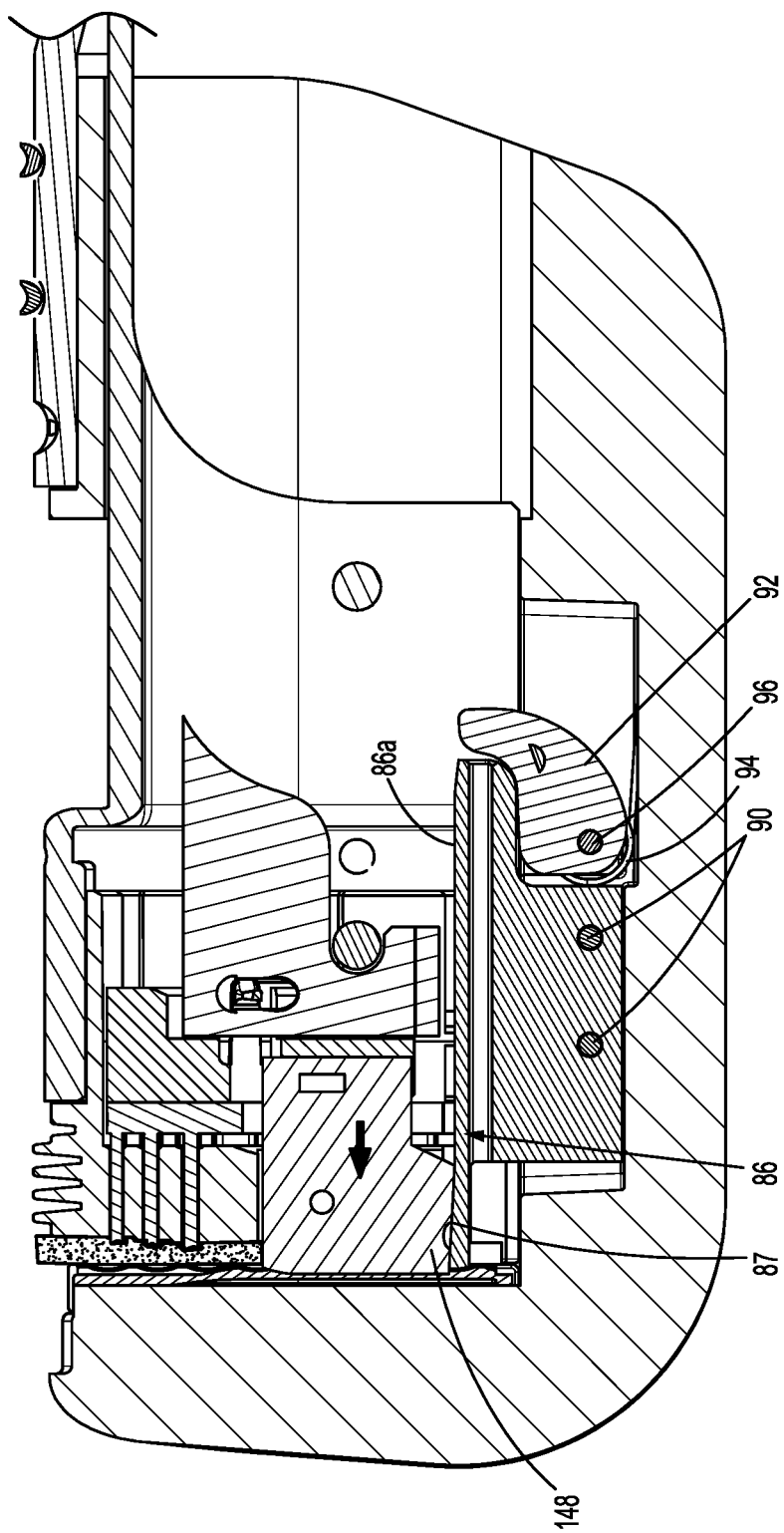
FIG. 19 is a cross-sectional view taken along section line 19-19 of FIG. 17.
Figure 23:
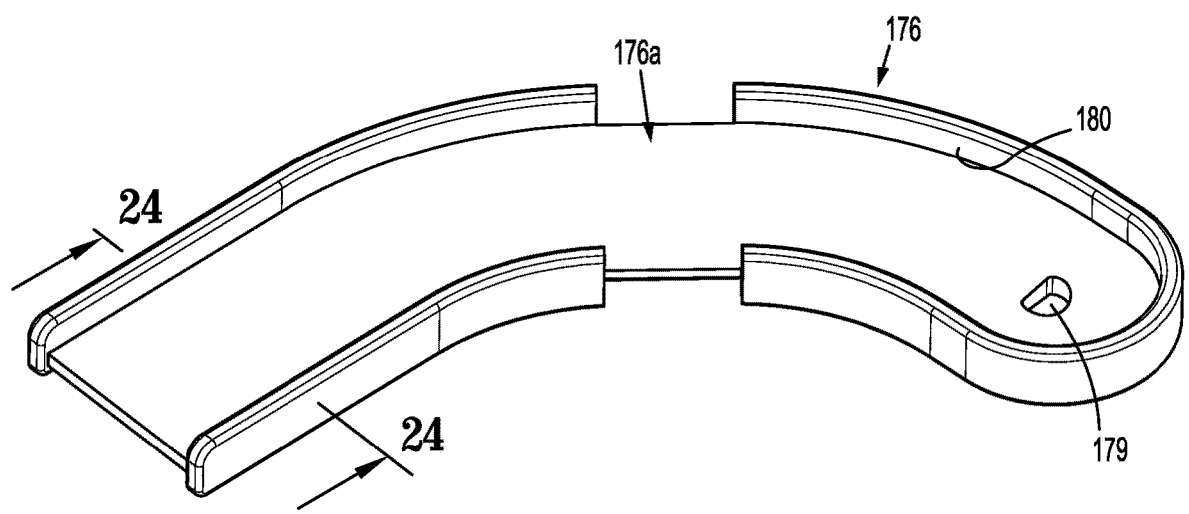
FIG. 23 is a perspective view from the proximal end of an alternative embodiment of the cutting plate of the tool assembly shown in FIG. 17.
Figure 24:
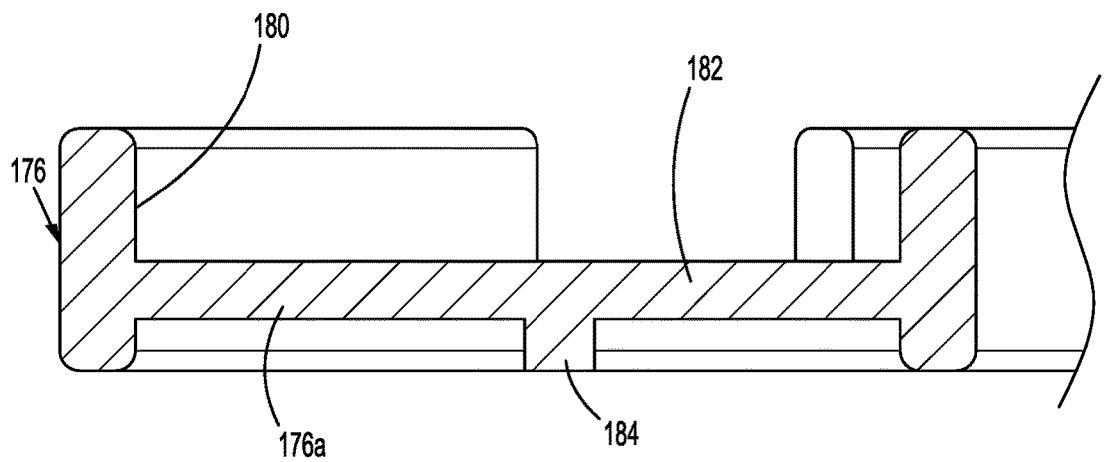
FIG. 24 is a cross-sectional view taken along section lines 24-24 of FIG. 23.

FIGS. 23 and 24 illustrate an alternate embodiment of the disclosed cutting plate shown generally as cutting plate 176. The cutting plate 176 includes a body 176a formed of a plastic material such as described above. The body 176a defines a recess 180 and an alignment pin bore 179. The recess 180 is configured to receive the distal transverse portion 68 of the U-shaped frame 60 of the tool assembly 16 and the alignment pin bore 179 is positioned to receive the alignment pin 120 (FIG. 18). The body 176a includes a central portion 182 that includes a raised ridge 184 that is in alignment with the knife slot 108 in the anvil plate 78. The central portion 182, except for the ridge 184, has a substantially uniform thickness.

Figure 26:
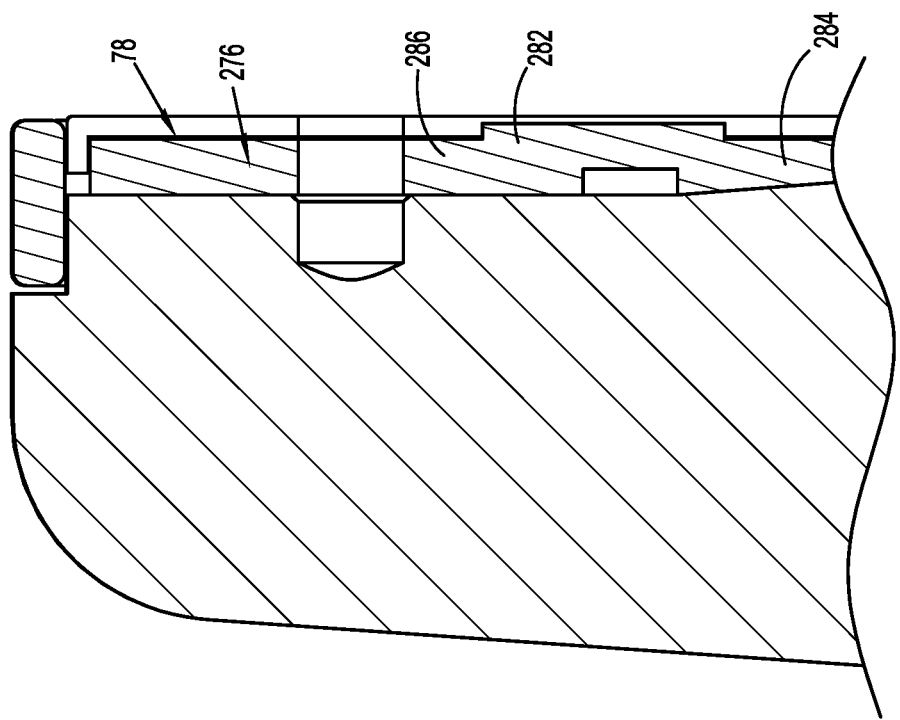
FIG. 26 is a cross-sectional view taken through a first jaw of the tool assembly shown in FIG. 17 including the anvil assembly and the cutting plate shown in FIG. 25.
Figure 25:
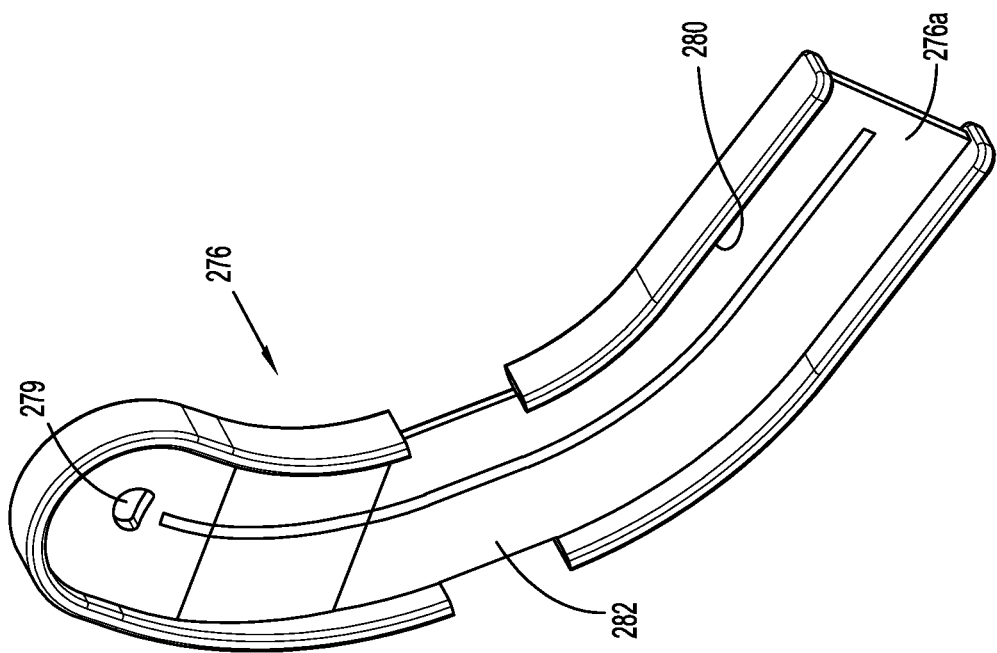
FIG. 25 is a perspective view from the proximal end of another alternative embodiment of the cutting plate of the tool assembly shown in FIG. 17.

FIGS. 25 and 26 illustrate another alternate embodiment of the disclosed cutting plate shown generally as cutting plate 276. The cutting plate 276 is similar to the cutting plate 176 and includes a body 276a that defines an alignment pin bore 279 and a recess 280. The recess 280 is configured to receive the distal transverse portion 68 (FIG. 5) of the frame 60 of the tool assembly 16 and the alignment pin bore 279 is positioned to receive the alignment pin 120 (FIG. 18). The body 276a includes a central portion 282 that has a thickness that increases through a transition portion 284 such that the end portion 286 of the cutting plate 276 which is spaced further from the longitudinal portion 70 of the frame 60, has a greater thickness than the portion of the body 276a that is closer to the longitudinal portion 70 of the frame 60. As is clear from the description above, the anvil assembly 62 of the tool assembly 16 is supported in cantilevered fashion on the distal transverse portion 68 of the frame 60. The increase in thickness of the cutting plate 276 at a location spaced from the longitudinal portion 70 of the frame 60 provides additional support to the anvil assembly 62 at a location spaced from the longitudinal portion 70 to limit deformation or deflection of the anvil assembly 62 during firing of the stapling device 10.

Figure 17:
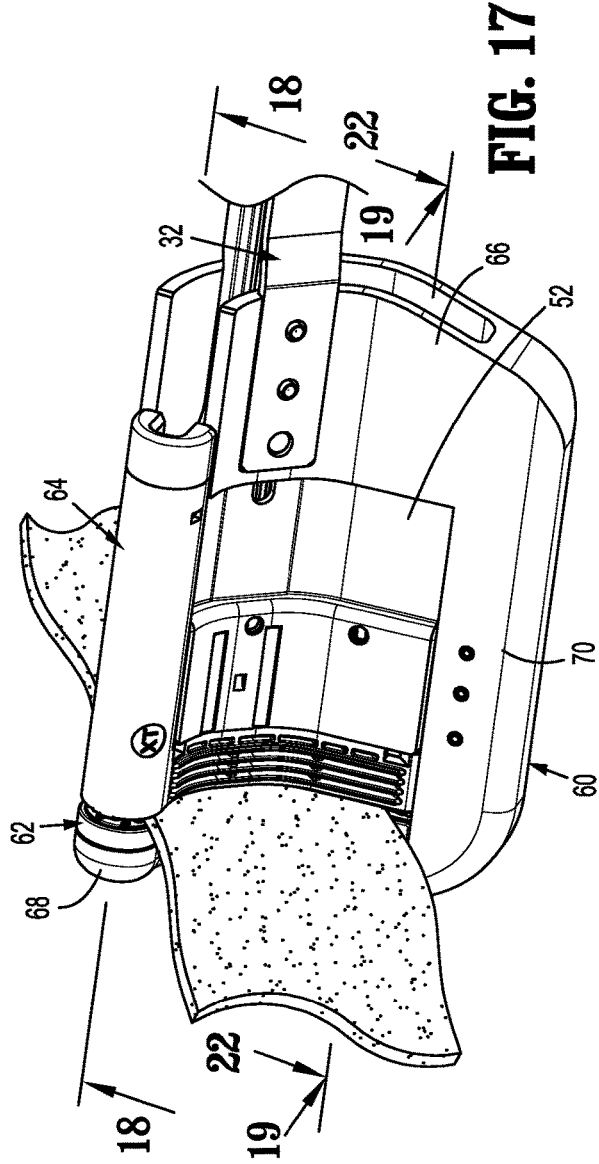
FIG. 17 is a side perspective view of the tool assembly of the stapling device shown in FIG. 1 in the clamped and fired positions clamped about tissue.

Referring briefly to FIGS. 16 and 17, when a cartridge assembly 64 including staples 106 is loaded into the cartridge receiving cavity 56 (FIG. 4) of the clamp slide assembly 52 in the direction indicated by arrow "X" with the tool assembly 16 in the unclamped position (FIG. 16), the thrust bar 142 engages the knife holder 100 and the pusher 104 of the cartridge assembly 64 engages the lockout member 92 to rotate the lockout member 92 in the direction indicated by arrow "A" in FIG. 16 to the unlocked position. In the unlocked position, the lockout member 92 is spaced downwardly below the thrust bar 142. As such, when the movable trigger 22 (FIG. 1) of the stapling device 10 is actuated to advance the clamp slide assembly 52 to the clamped position (FIG. 17), the thrust bar 142 can move distally beyond the lockout member 92 to actuate the tool assembly 16 and advance the knife 102 and the pusher 104 to staple and cut tissue.

Figure 28:
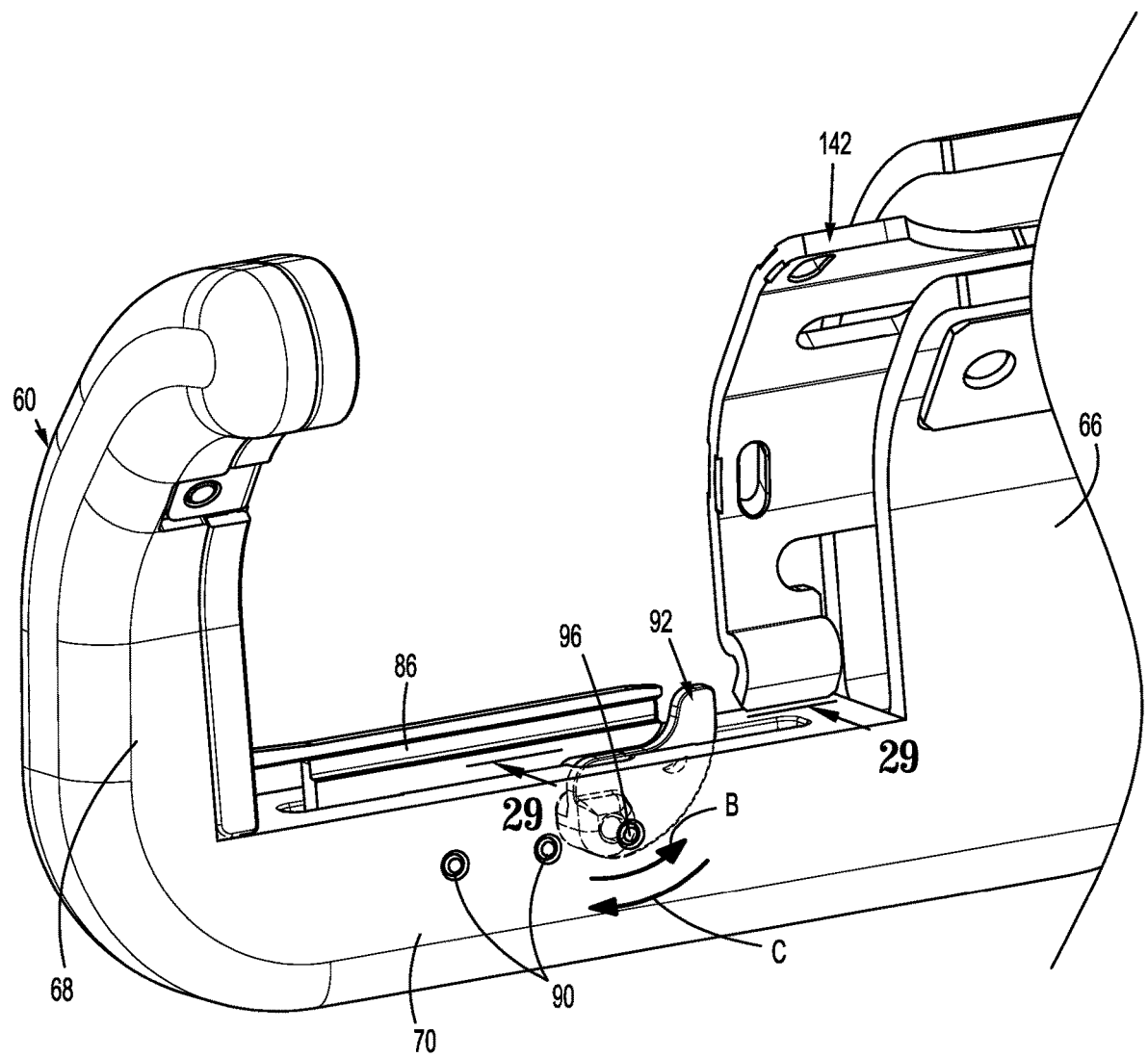
FIG. 28 is a side perspective view of a frame of the tool assembly of the stapling device shown in FIG. 1 with the cartridge assembly removed and the lockout member in a locked position.
Figure 29:
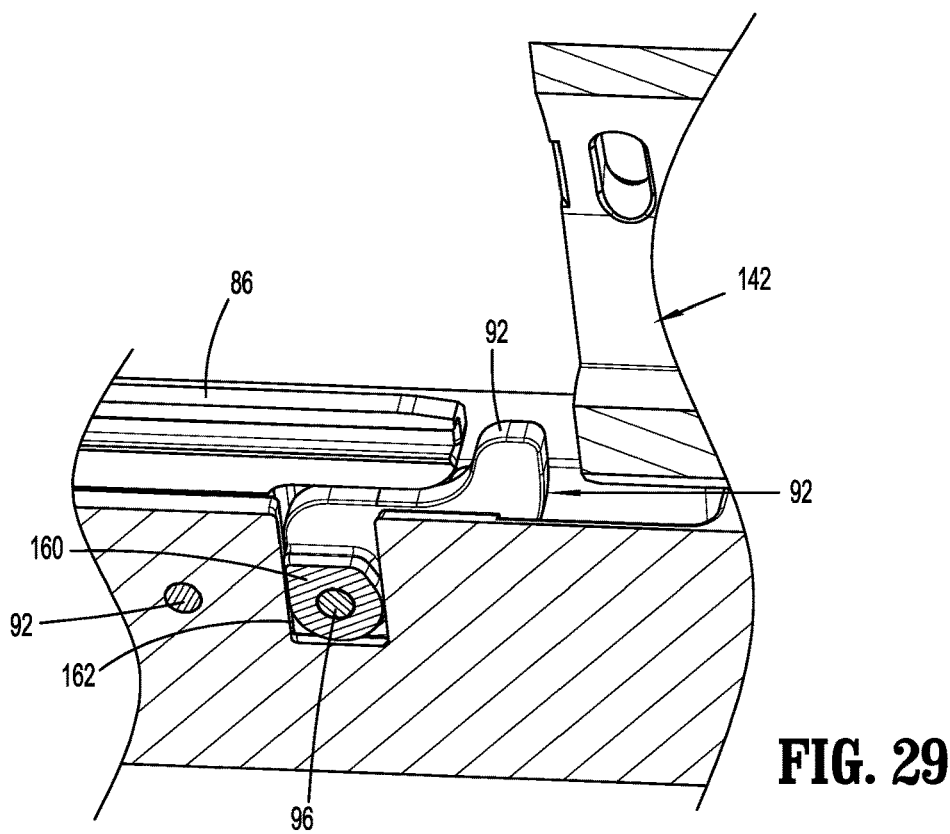
FIG. 29 is a cross-sectional view taken along section lines 29-29 of FIG. 28.
Figure 30:
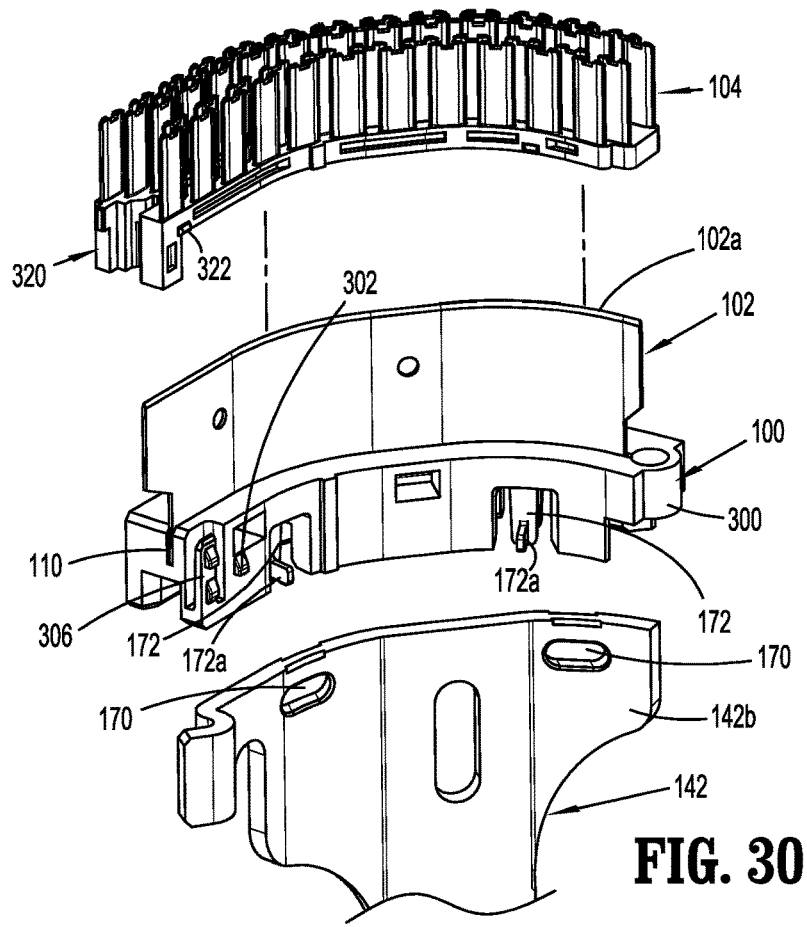
FIG. 30 is a side perspective view of a distal portion of a thrust bar, knife holder, and pusher of the stapling device shown in FIG. 2 with parts separated.
Figure 31:
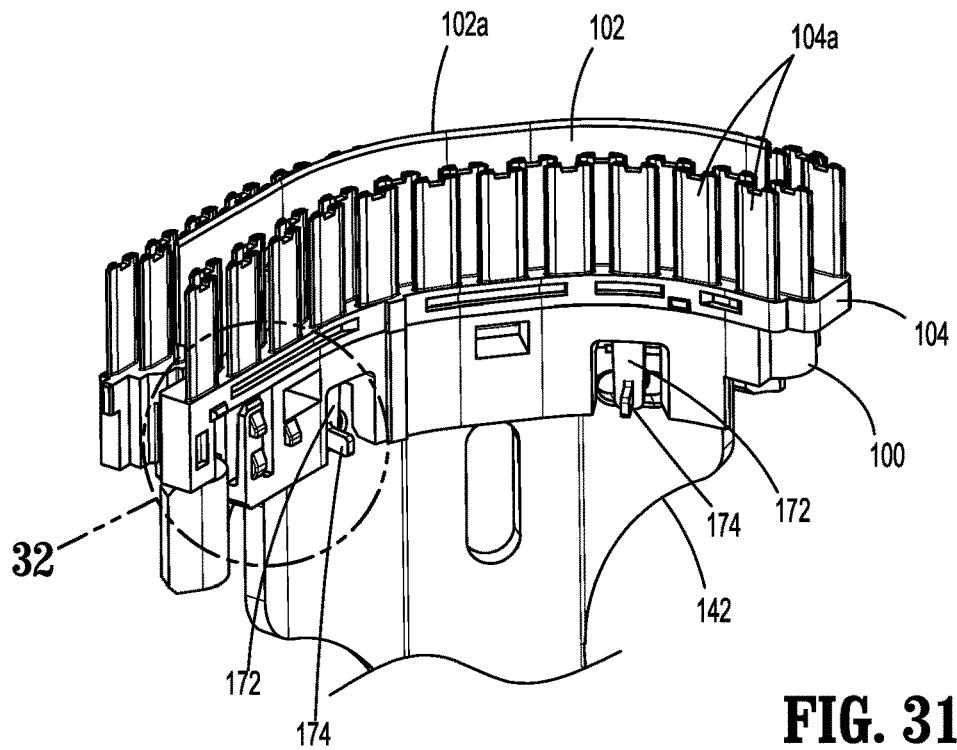
FIG. 31 is a side perspective view of the distal portion of the thrust bar shown in FIG. 30 supporting the knife holder and the pusher.
Figure 39:
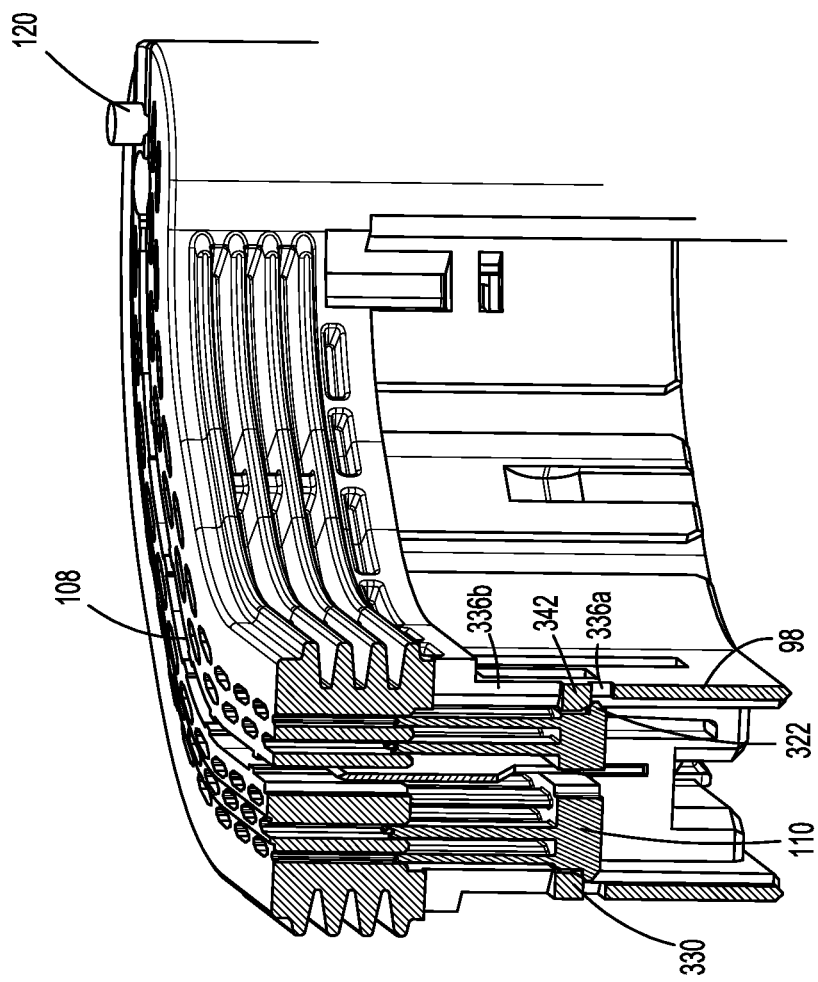
FIG. 39 is a side cross-sectional view taken through a second portion of the cartridge assembly shown in FIG. 36A with the cartridge assembly in a pre-fired position.
Figure 43:
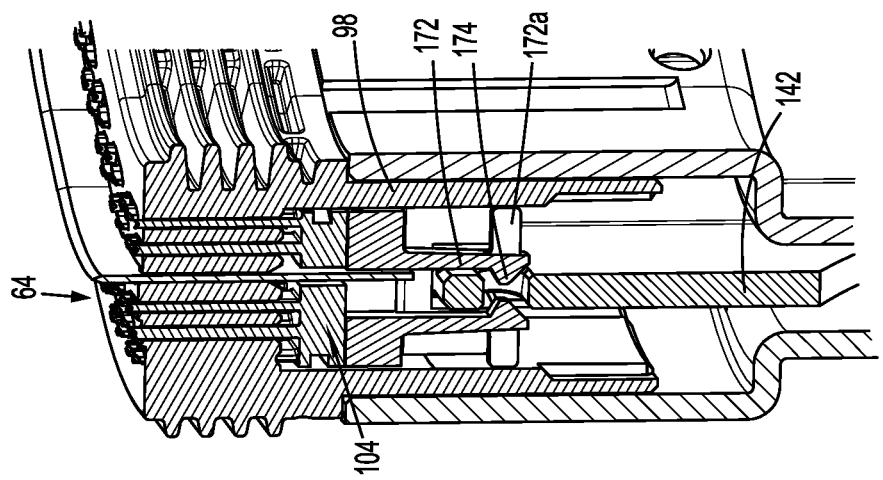
FIG. 43 is a side cross-sectional view taken through a second portion of the cartridge assembly shown in FIG. 40 with the cartridge assembly in a fired position.
Figure 42:
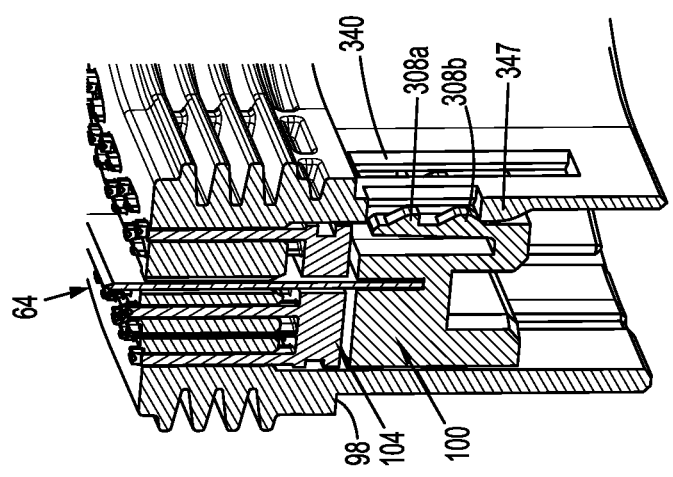
FIG. 42 is a side cross-sectional view taken through a first portion of the cartridge assembly shown in FIG. 39 with the cartridge assembly in a fired position.

Referring to FIGS. 27-29, when the cartridge assembly 64 is removed from the cartridge receiving cavity 56 of the clamp slide assembly 52 or the pusher 104 (FIG. 16) is moved to its advanced or fired position (FIG. 39), the biasing member 94 of the lockout assembly 88 rotates the lockout member 92 about the pivot member 96 in the direction indicated by arrow "B" in FIG. 28 to a position obstructing distal movement of the thrust bar 142 beyond the locking member 92. It is noted that engagement of the thrust bar 142 with the lockout member 92 during movement of the thrust bar 142 from its advanced position back towards its retracted position causes rotation of the lockout member 92 about the pivot member 96 in the direction indicated by arrow "C" back to its unlocked position to allow the thrust bar 142 to pass proximally over the lockout member 92. However, the lockout member 142 includes a stop member 160 that is received in a recess 162 (FIG. 29) formed in the longitudinal portion 70 of the frame 60. The recess 162 is dimensioned to prevent rotation of the lockout member 92 in the direction "B" beyond a predetermined point to prevent distal movement of the thrust bar 142 when the lockout member 92 is in the locked position. More specifically, when the lockout member 92 is urged to the locked position by the biasing member 94 (FIG. 15), re-advancement of the thrust bar 142 is prevented by the lockout member 92.

Referring to FIGS. 30-34, the distal portion 142b of the thrust bar 142 defines first and second spaced openings 170 and the knife holder 100 includes two pairs of resilient fingers 172 that are spaced transversely from each other. Each pair of resilient fingers 172 is aligned with one of the openings 170 of the thrust bar 142 when the cartridge assembly 64 is loaded into the cartridge receiving cavity 56 of the clamp slide assembly 52. The resilient fingers 172 include an inwardly extending protrusions 174 (FIG. 33) that pass over the distal portion 142b of the thrust bar 142 when a cartridge assembly 64 is loaded into the tool assembly 16 and snap into the openings 170 in the thrust bar 142 (FIG. 31) to couple the thrust bar 142 to the knife holder 100. Each of the resilient fingers 172 includes diametrically opposed spacers 172a that engage an inner wall of the housing 98 of the cartridge assembly 64 to ensure that the protrusions 174 of the resilient fingers 172 do not become disengaged from openings 170 in the thrust bar 142 during operation of the stapling device 10.

Figure 32:
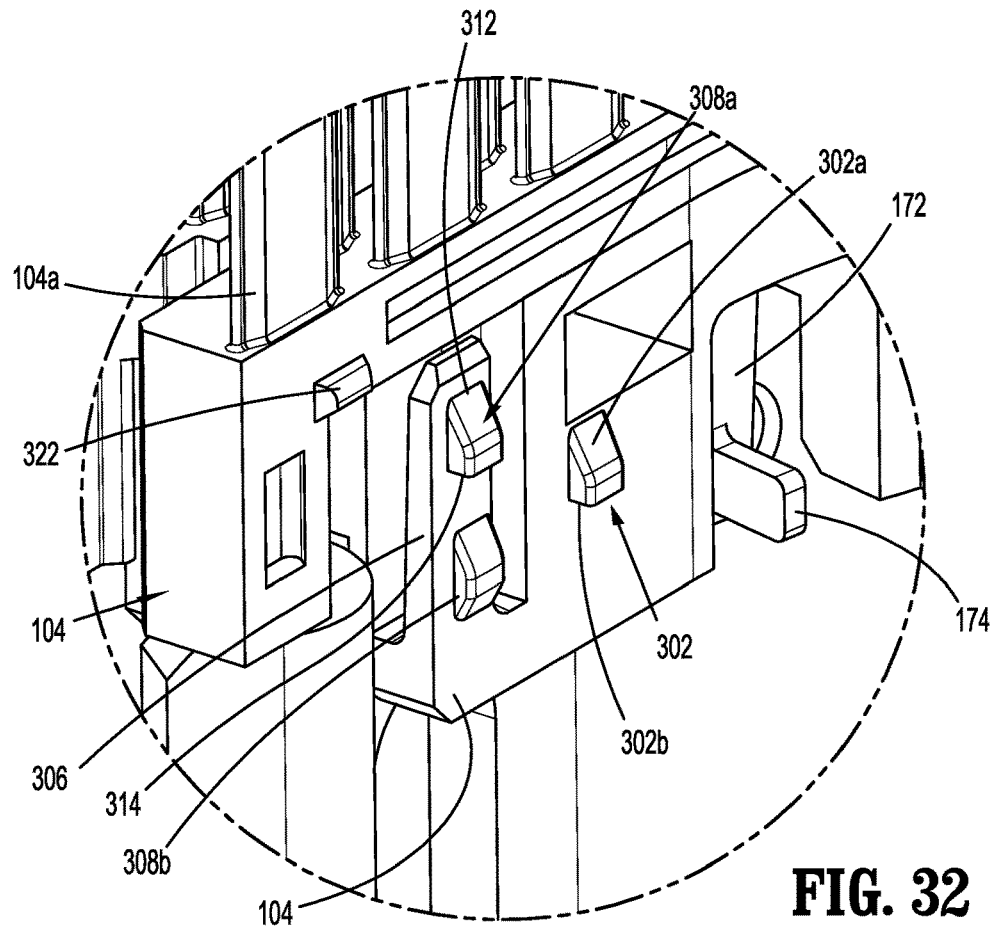
FIG. 32 is an enlarged view of the indicated area of detail shown in FIG. 31.
Figure 33:
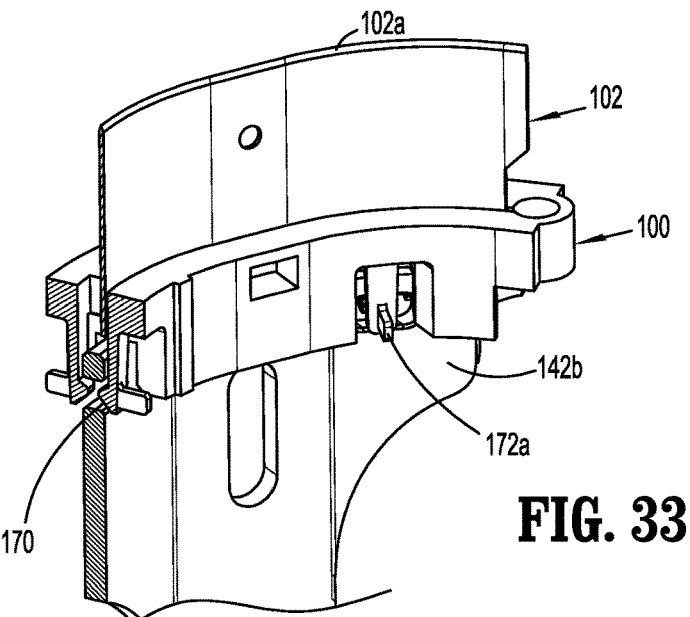
FIG. 33 is a side perspective cross-sectional view of the thrust bar coupled to the knife holder shown in FIG. 31.

In some embodiments, the knife holder 100 includes a body 300 that includes at least one retaining protrusion 302 and a resilient arm 306. The at least one retaining protrusion 303 includes a tapered distal face 302a (FIG. 32) and a proximal shoulder 302b. The resilient arm 306 has a pair of longitudinally spaced protrusions 308a and 308b (FIG. 32). In embodiments, the protrusion 308b is positioned proximally of the protrusion 308a and includes tapered distal and proximal surfaces 310. In contrast, the protrusion 308a is positioned distally of protrusion 308b and includes a tapered distal face 312 and a proximal shoulder or stop surface 314. Each of these protrusions 308a, 308b will be described in further detail below. In embodiments, the pusher 104 includes a body 320 having one or more spaced protrusions or bumps 322 that project outwardly from the body 320 and are positioned one or both sides of the pusher 104.

Figure 34:
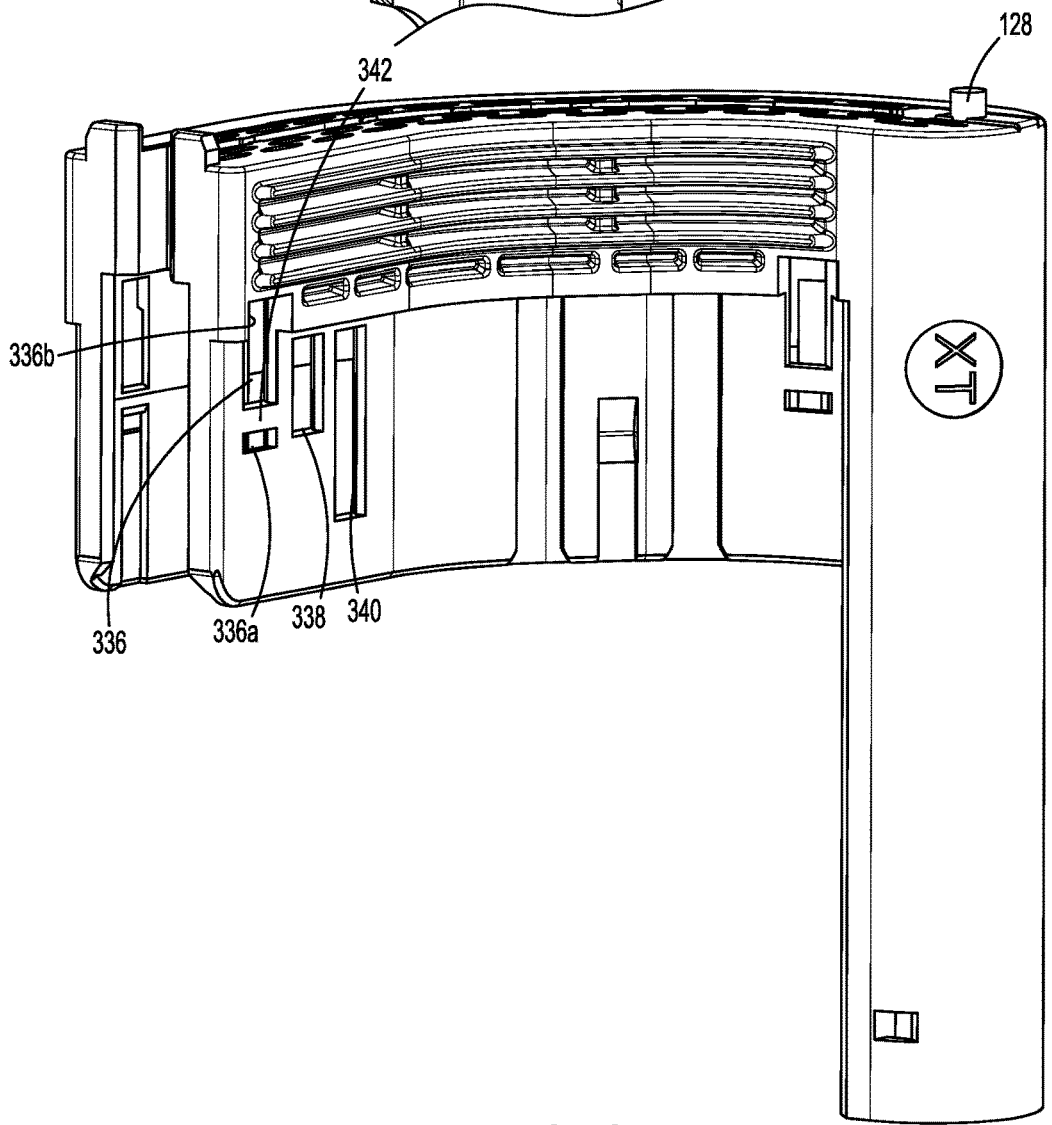
FIG. 34 is a side perspective view of a housing of the cartridge assembly of the stapling device shown in FIG. 1.
Figure 36A:
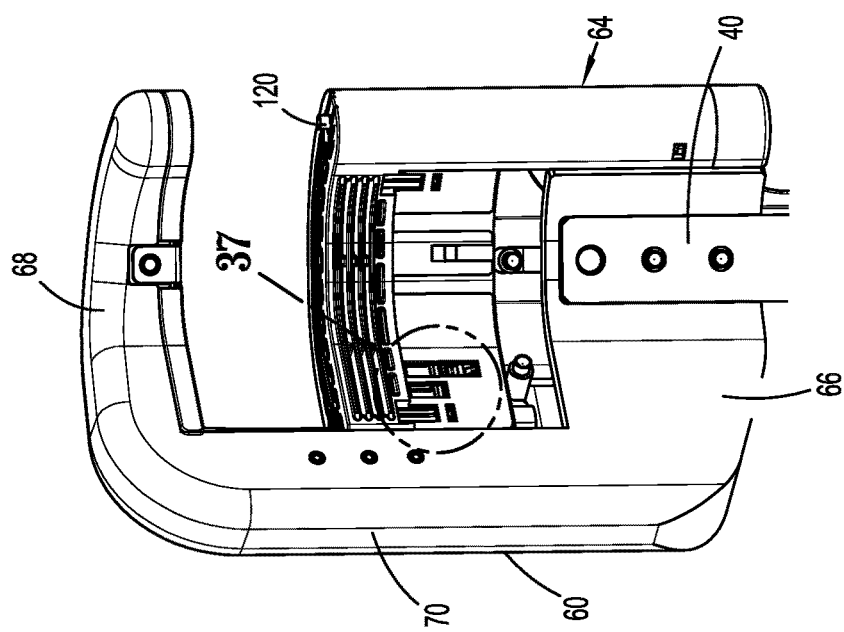
FIG. 36A is a side perspective view of the tool assembly of the stapling device shown in FIG. 1 in the pre-fired unclamped position.
Figure 36:
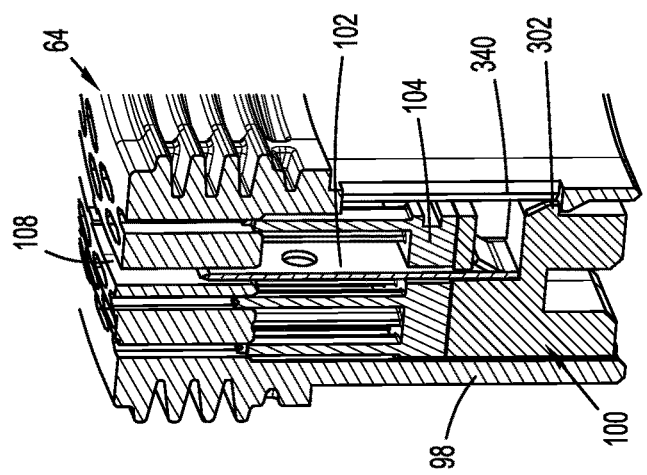
FIG. 36 is a cross-sectional view taken through the cartridge assembly shown in FIG. 35 with the cartridge assembly in a pre-fired unclamped position.

FIG. 34 illustrates the housing 98 of the cartridge assembly 64. In embodiments, the housing 98 of the cartridge assembly 64 defines a first longitudinal slot 336, a second longitudinal slot 338, and a third longitudinal slot 340. A divider or bridge 342 extends across the first longitudinal slot 336 to divide the slot 336 into a proximal portion 336a and a distal portion 336b. An inner wall of the housing 98 of the cartridge assembly 64 includes ramped abutments 346 (FIG. 35) and 347 (FIG. 36). The ramped abutments 346 and 347 have proximally facing ramped surface 346a, 347a, respectively. A distal end of the ramped abutment 346 is defined by a proximal end of the third longitudinal slot 340, and a distal end of the ramped abutment 347 is defined by a proximal end of the second longitudinal slot 338.

Figure 35:
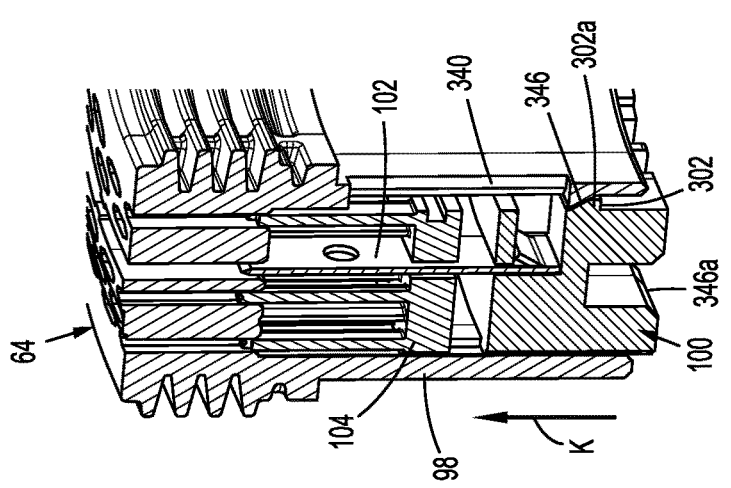
FIG. 35 is a cross-sectional view taken through the cartridge assembly of the stapling device shown in FIG. 1 as the knife holder is inserted into a housing of the cartridge assembly.
Figure 38:
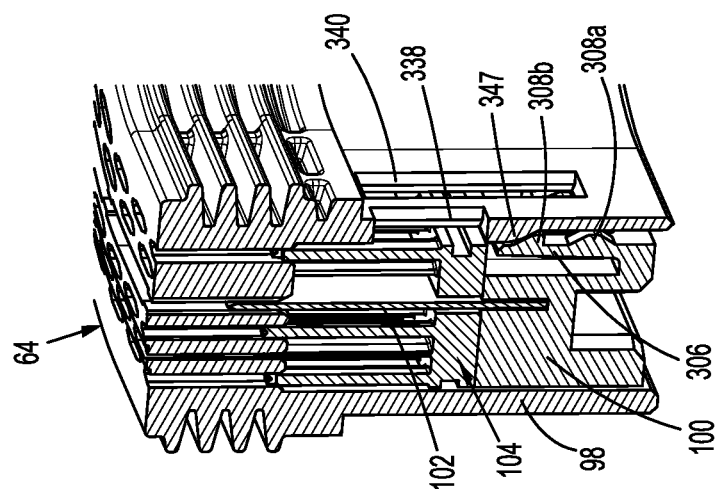
FIG. 38 is a side cross-sectional view taken through a first portion of the cartridge assembly shown in FIG. 36A with the cartridge assembly in a pre-fired position.

When the knife holder 100 is inserted through a proximal end of the housing 98 of the cartridge assembly 64 as indicated by arrow "K" in FIG. 35 during assembly of the cartridge assembly 64, the tapered distal face 302a of the retaining protrusion 302 formed on the body 300 of the knife holder 100 engages the proximally facing ramped surface 346a of the ramped abutment 346, passes over the ramped abutment 346, and snaps into the third longitudinal slot 346. The receipt of the retaining protrusion 302 within the longitudinal slot 346 retains the knife holder 100 within the cartridge housing 98.

Figure 37:
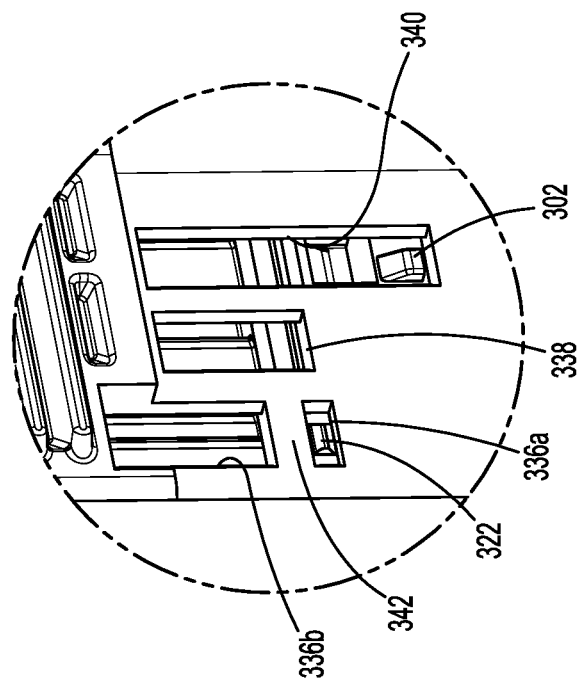
FIG. 37 is an enlarged view of the indicated area of detail shown in FIG. 36A.
Figure 40:
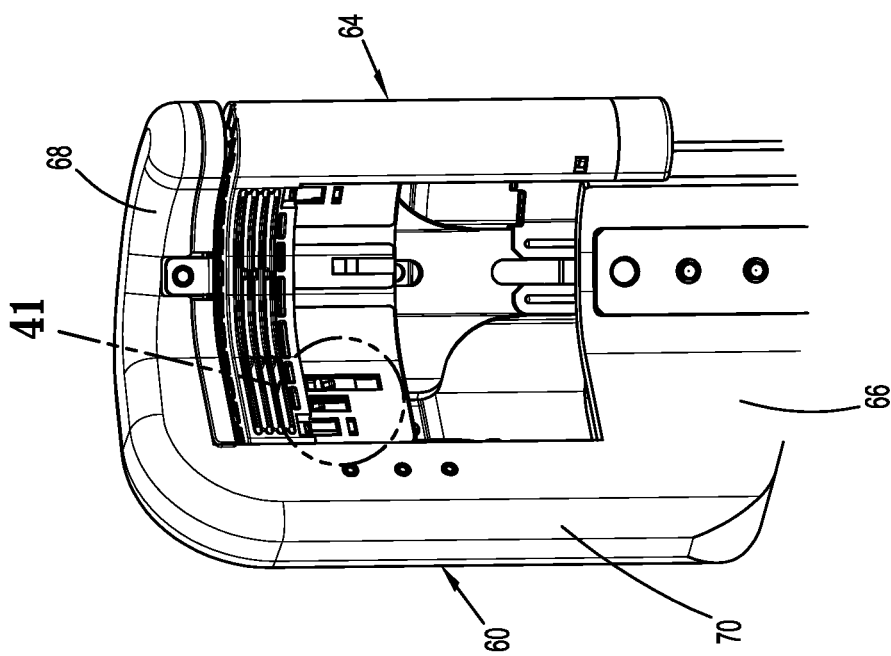
FIG. 40 is a side perspective view of the tool assembly of the stapling device shown in FIG. 1 in the pre-fired clamped position.

FIGS. 36-39 illustrate the cartridge assembly 64 in a pre-fired position. In this position, the retaining protrusion 302 of the body 300 of the knife holder 100 is received within the proximal end of the third longitudinal slot 340 to prevent proximal movement of the knife holder 100 within the housing 98 of the cartridge assembly 64. The protrusion 322 formed on the body 320 of the pusher 104 is received in the proximal portion 336a of the first longitudinal slot 336 (FIG. 37). In this position, the divider 342 that extends across the first longitudinal slot 336 is engaged with the protrusion 322 (FIG. 39) to obstruct distal movement of the pusher 104 within the cartridge housing 98. This prevents inadvertent movement of the pusher 104 during shipping and storage of the cartridge assembly 64.

In the pre-fired position, the tapered distal surface of the protrusion 308b of the resilient arm 306 on the knife holder 100 is engaged with the ramped abutment 347 (FIG. 38) formed on the inner wall of the housing 98 of the cartridge assembly 64 to obstruct distal movement of the knife holder 100 within the housing 98. This engagement prevents inadvertent movement of the knife holder 100 during shipping and storage of the cartridge assembly 64.

Figure 41:
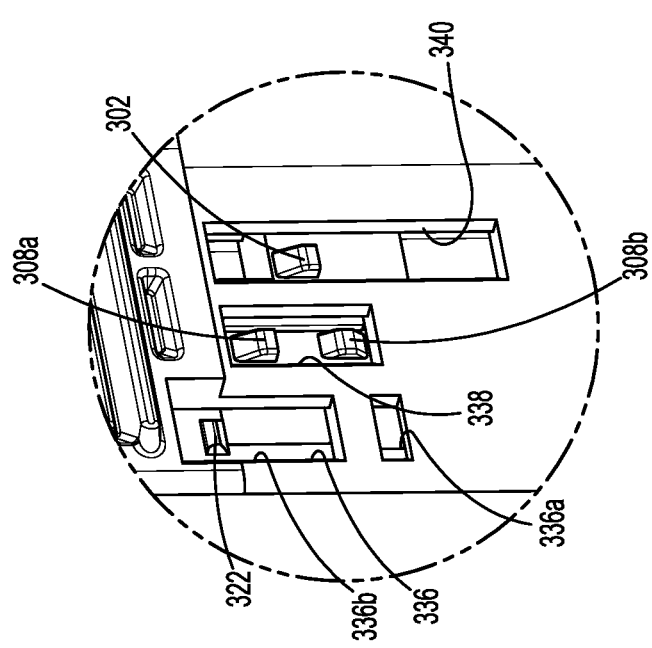
FIG. 41 is an enlarged view of the indicated area of detail shown in FIG. 40.

FIGS. 40-43 illustrate the cartridge assembly 64 in a fired position. More specifically, when the movable trigger 22 (FIG. 1) is actuated to advance the thrust bar 142 (FIG. 2) to fire staples 106 from the cartridge assembly 64, the thrust bar 142 advances the knife holder 100 within the housing 98 of the cartridge assembly 64 from its retracted position to its advanced position. As the knife holder 100 moves from its retracted position towards its advanced position within the housing 98, the knife holder 100 engages the pusher 104 and advances the pusher 104 within the housing 98. As the knife holder 100 moves towards its advanced position, the spaced protrusions 308a and 308b formed on the resilient arm 306 of the knife holder 100 pass over the ramped abutment 347 formed on an inner surface of the housing 98 and snap into the second longitudinal slot 338 formed in the housing 98 (FIG. 41). In the advanced position of the knife holder 100 (FIGS. 41 and 42), the protrusions 308a and 308b are positioned in the second longitudinal slot 338. In addition, the retaining protrusion 302 formed on the body 300 of the knife holder 100 moves from a proximal end portion of the third longitudinal slot 340 to a distal end portion of the third longitudinal slot 340 (FIG. 41). As the knife holder 100 moves within the housing 98 of the cartridge assembly 64, the knife 102 which is supported on the knife holder 100 is advanced through the knife slot 108 in the housing 98 of the cartridge assembly 64 and into engagement with the cutting plate 76 of the anvil assembly 62 to cut tissue positioned between the cartridge assembly 64 and the anvil assembly 62.

When the pusher 104 is moved by the knife holder 100 within the housing 98 of the cartridge assembly 64, the protrusion 322 on the body 320 of the pusher 104 moves from a proximal end portion of the first longitudinal slot 336 to a distal end portion of the first longitudinal slot 336 (FIG. 41). As the pusher 104 moves towards its advanced position, the fingers 104a of the pusher 104 advance the staples 106 (FIG. 16) into the anvil assembly 62 to form the staples within the tissue.

FIGS. 44-47 illustrate the cartridge assembly 64 after the cartridge assembly 64 is fired and the thrust bar 142 is retracted. When the thrust bar 142 is retracted, the knife holder 100, which is coupled to the thrust bar 142 by the protrusions 174 (FIG. 48) on the resilient fingers 172 of the knife holder 100, is also retracted within the housing 98 of the cartridge assembly 64. As the knife holder 100 is retracted within the housing 98, the protrusion 308b on the knife holder 100 moves into engagement with and passes over the ramped abutment 347 formed on the inner wall of the housing 98 such that the protrusion 308b is positioned on a proximal side of the ramped abutment surface 347 and the protrusion 308a is positioned on a distal side of the ramped abutment surface 347 (FIG. 46). The engagement of the protrusions 308a and 308b with the ramped abutment surface 347 retains the knife holder 100 in a retracted position within the housing 98 of the cartridge assembly 64 such that the knife 102 including the cutting edge 102a is recessed within the housing 98.

Figure 47:
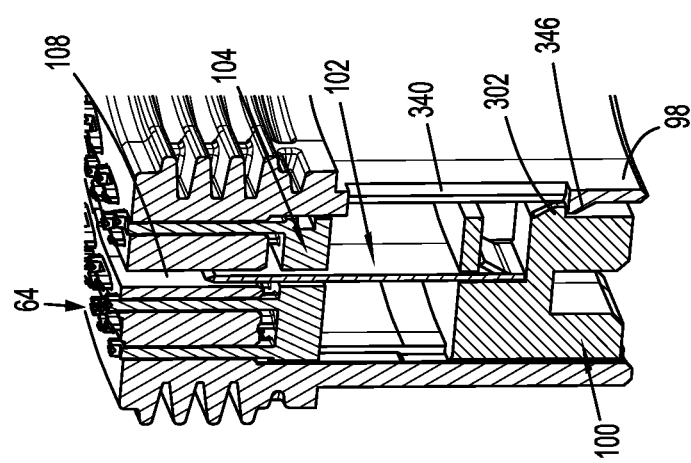
FIG. 47 is a side cross-sectional view taken through a second portion of the cartridge assembly with the cartridge assembly in a fired unclamped position.
Figure 49:
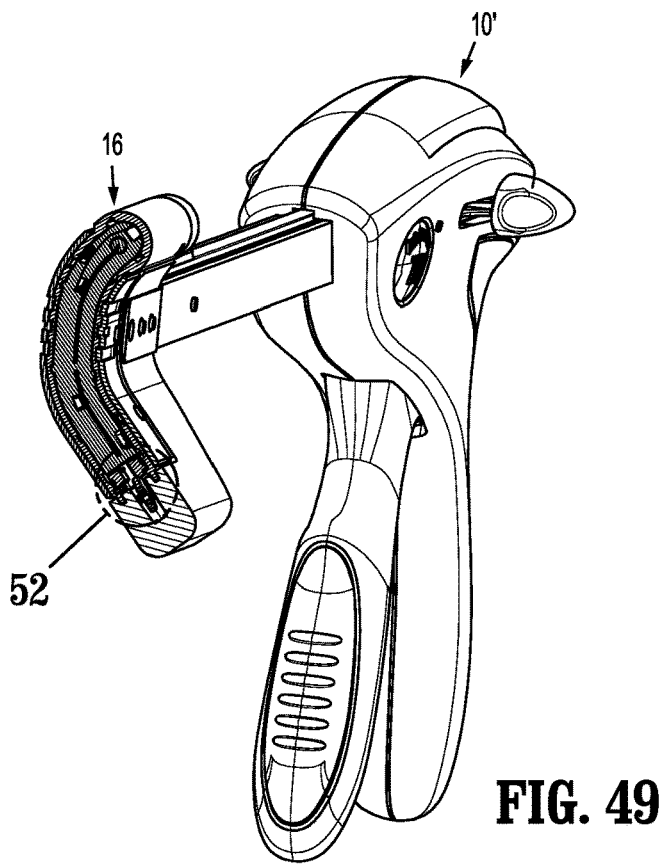
FIG. 49 is a side perspective partial cross-sectional view through the tool assembly of an alternate embodiment of the disclosed stapling device.
Figure 50:
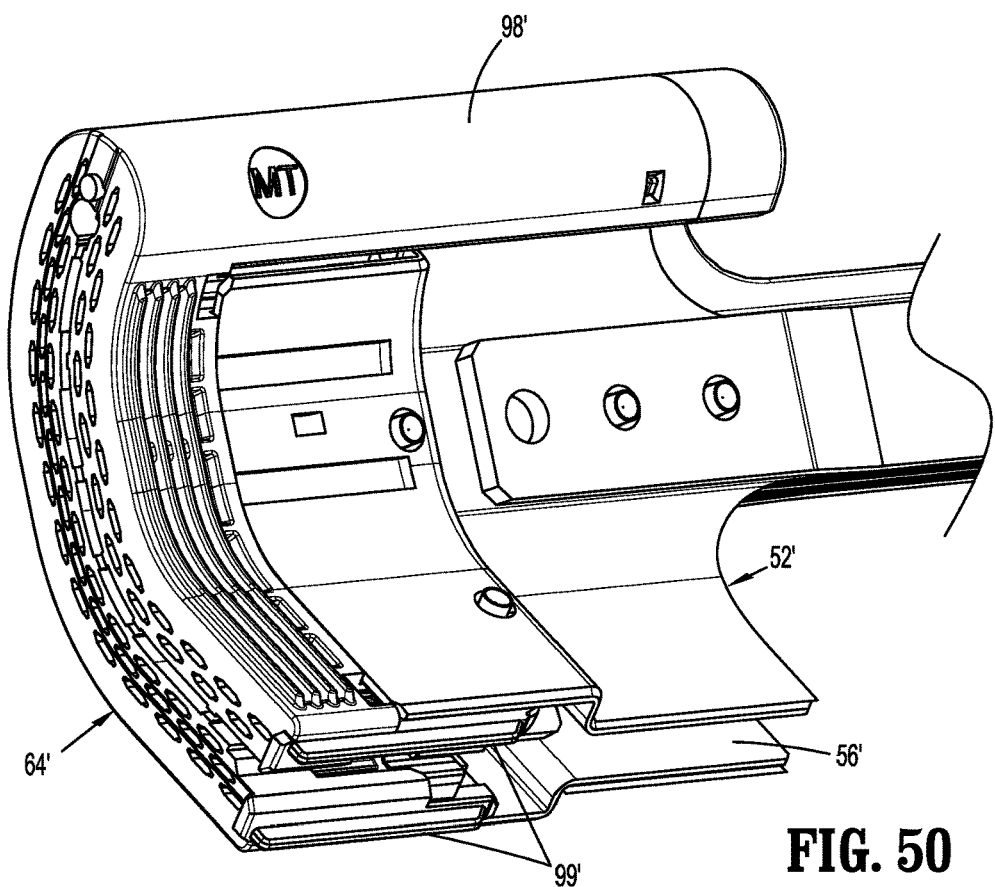
FIG. 50 is a side perspective view of the clamp slide assembly and cartridge assembly of the stapling device shown in FIG. 49.
Figure 51:
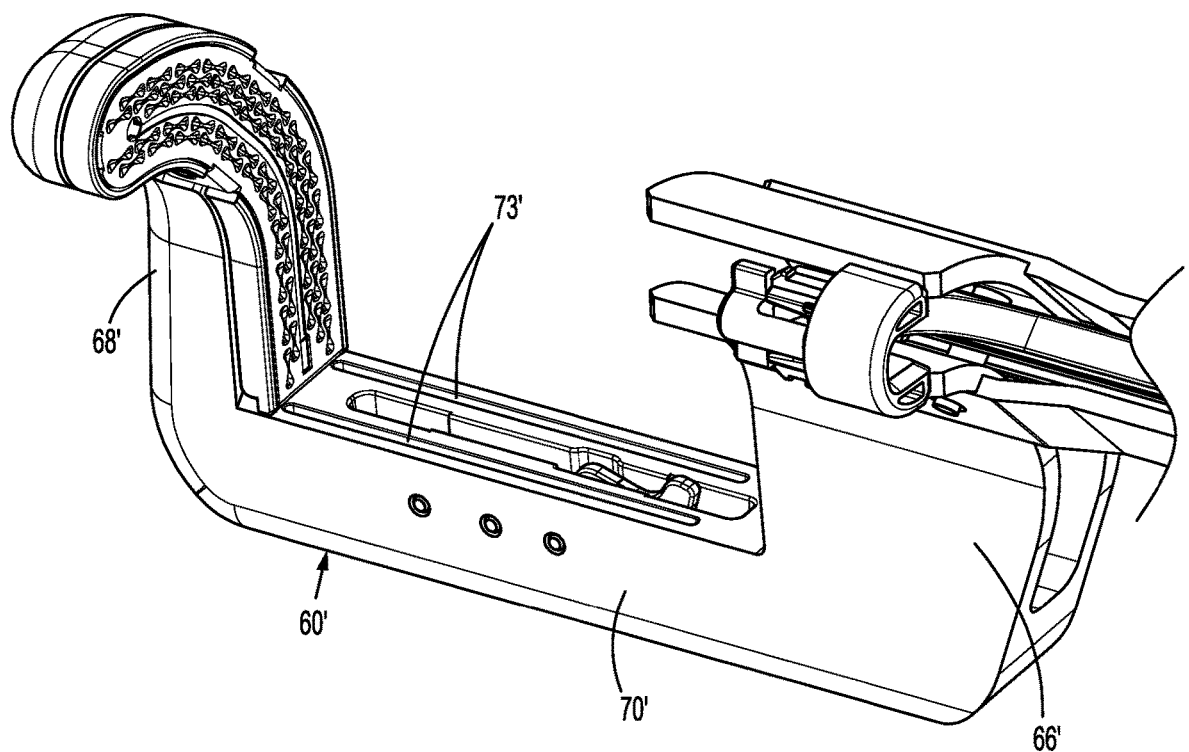
FIG. 51 is a side perspective view of the distal portion of the stapling device shown in FIG. 49 with the cartridge assembly removed from the clamp slide assembly.
Figure 52:
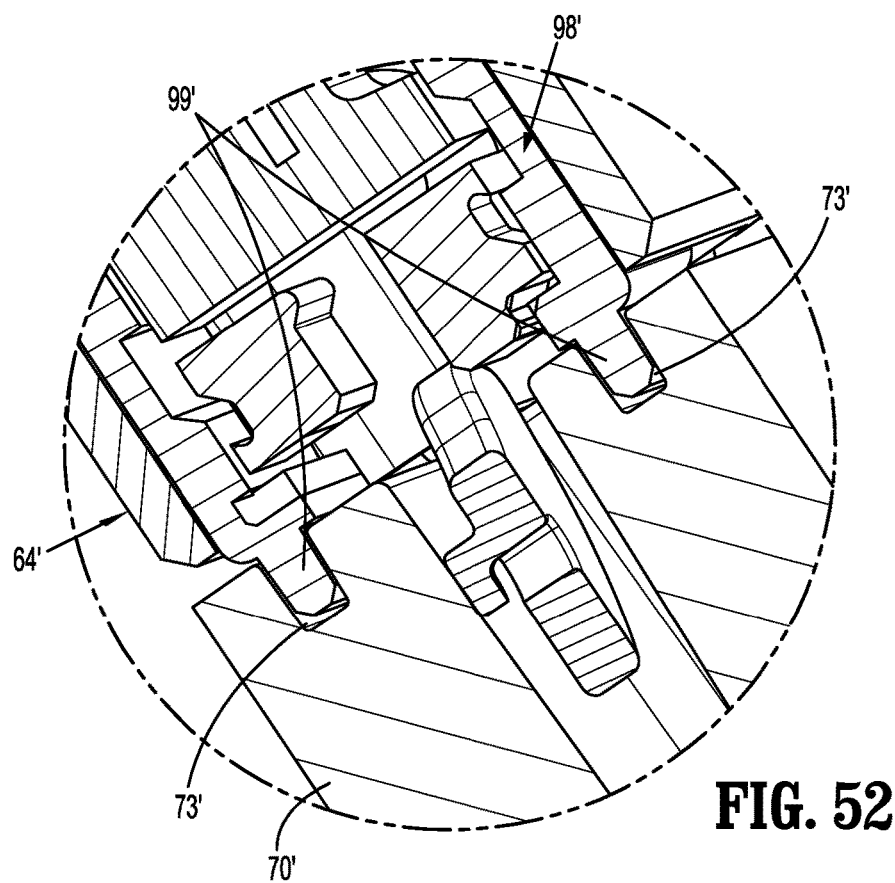
FIG. 52 is an enlarged view of the indicate area of detail shown in FIG. 49.

As the knife holder 100 is retracted within the housing 98 of the cartridge assembly 64, the retaining protrusion 302 on the body 300 of the knife holder 100 moves within the third longitudinal slot 340 such that the proximal shoulder 302b of the protrusion 302 engages the portion of the housing 98 that defines the proximal end of the third longitudinal slot 340 to further prevent proximal movement of the knife holder 100 within the housing 98 of the cartridge assembly 64 (FIG. 47).

Figure 48:
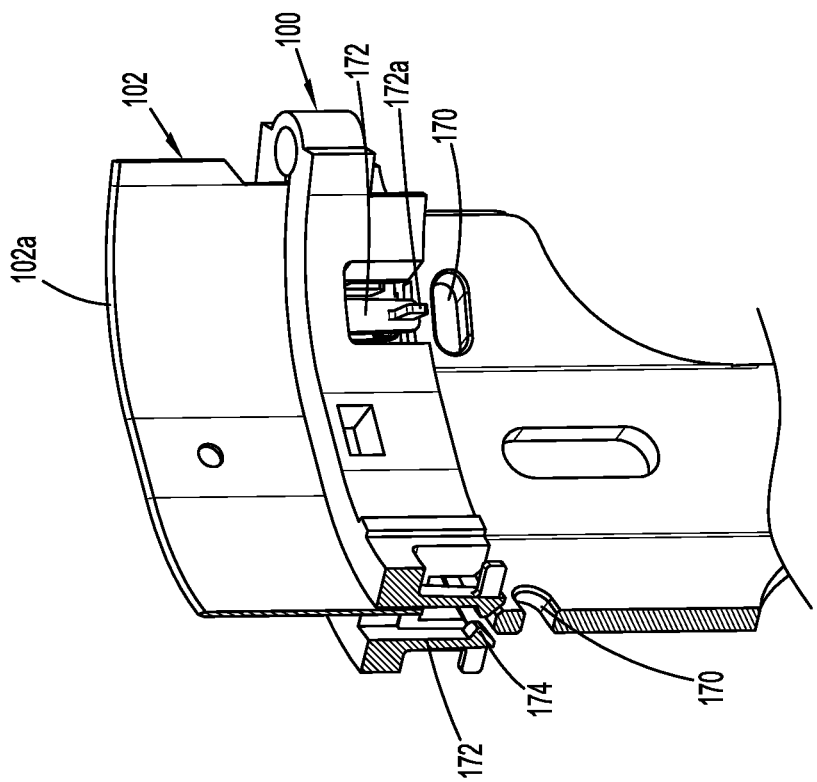
FIG. 48 is side perspective cross-sectional view of the thrust bar and knife holder of the cartridge assembly of the stapling device shown in FIG. 1 as the thrust bar is separated from the knife holder.

Referring to FIG. 48, when the thrust bar 142 is moved to its fully retracted position, the thrust bar 142 will separate from the knife holder 100 to facilitate removal of the cartridge assembly 64 from cartridge receiving cavity 56 of the clamp slide assembly 52. This occurs because proximal movement of the knife holder 100 is stopped via engagement of the proximal shoulder 302b of the protrusion 302 with the housing 98 prior to the thrust bar 142 reaching its fully retracted position.

FIGS. 49-52 illustrate an alternate embodiment of the disclosed stapling device shown generally as stapling device 10'. The stapling device 10' is substantially similar to stapling device 10 in all respects except for modifications to the cartridge assembly 64' and the U-shaped frame 60' of the tool assembly 16' which are described in detail below.

The U-shaped frame 60' of the tool assembly 16' includes a proximal transverse portion 66', a distal transverse portion 68', and a longitudinal portion 70' interconnecting the proximal transverse portion 66' and the distal transverse portion 68'. The longitudinal portion 70' of the U-shaped frame 60' defines spaced longitudinal slots 73'. The cartridge assembly 64' includes a housing 98' that supports or includes ribs 99' that are positioned to be received within the longitudinal slots 73' when the cartridge assembly 64' is loaded within the cartridge receiving cavity 56' (FIG. 50) of the clamp slide assembly 52' of the stapling device 10'. When the cartridge assembly 64' is moved in relation to the anvil assembly 62 from the unclamped position to the clamped position, the ribs 99' of the housing 98' of the cartridge assembly 64' slide within the longitudinal slots 73' to guide and provide rigidity to the cartridge assembly 64'.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

The invention claimed is:
1. A surgical stapling device comprising:
an elongate body defining a longitudinal axis, the elongate body having a proximal portion and a distal portion; and
a tool assembly supported on the distal portion of the elongate body, the tool assembly including an anvil assembly, a cartridge assembly, and a U-shaped frame, the U-shaped frame having a distal frame portion extending transverse to the longitudinal axis, a proximal frame portion extending transverse to the longitudinal axis, and a longitudinal frame portion extending between the distal frame portion and the proximal frame portion, the anvil assembly supported on the distal frame portion and including an anvil plate;

the cartridge assembly supported between the proximal frame portion and the distal frame portion and being movable in relation to the anvil assembly from a retracted position in which the cartridge assembly is spaced from the anvil assembly to an advanced position in which the cartridge assembly is in juxtaposed alignment with the anvil assembly, the cartridge assembly including a housing defining a cavity, a staple pusher positioned within the cavity, a knife holder positioned within the cavity, a knife supported on the knife holder, and an alignment pin, the knife including side edges, and a cutting edge that extends in a direction transverse to the longitudinal axis;

the alignment pin supported within the housing of the cartridge assembly at a position spaced from the longitudinal frame portion, the alignment pin movable between a retracted position recessed within the housing and an advanced position extending from the housing into engagement with the anvil assembly, the alignment pin including a guide surface that faces the longitudinal portion of the U-shaped frame, the guide surface having a distal portion that is angled towards the longitudinal portion, the knife being movable from a retracted position recessed within the housing to an advanced position extending from the housing, wherein a first side edge of the side edges of the knife is positioned to move along the guide surface of the alignment pin such that engagement of the first side edge of the knife with the distal portion of the guide surface compresses the first side edge of the knife.

2. The surgical stapling device of claim 1, wherein the tool assembly includes a guide plate supported on the longitudinal portion of the U-shaped frame, the guide plate having a guide surface including a distal portion that is angled inwardly away from the longitudinal portion of the U-shaped frame towards the alignment pin, a second side edge of the side edges of the knife positioned to move along the guide surface of the guide plate such that engagement of the second side edge of the knife with the distal portion of the guide surface of the guide plate compresses the second side edge of the knife.

3. The surgical stapling device of claim 2, wherein the knife has a first wing on the first side edge of the knife and a second wing on the second side edge of the knife, the first wing positioned to engage the guide surface of the alignment pin and the second wing positioned to engage the guide surface of the guide plate.

4. The surgical stapling device of claim 1, further including a handle assembly, wherein the elongate body extends distally from the handle assembly.

5. The surgical stapling apparatus of claim 1, wherein the anvil assembly includes an anvil plate and a cutting plate supported on the distal frame portion of the U-shaped frame of the tool assembly, the anvil plate positioned to receive and deform the staples and the cutting plate positioned to engage the knife.

6. The surgical stapling device of claim 5, wherein the cutting plate is sandwiched between the distal frame portion and the anvil plate, and the anvil plate defines a knife slot to facilitate passage of the knife through the anvil plate.

7. The surgical stapling device of claim 6, wherein the cutting plate is formed from a plastic material selected from the group consisting of a polyether ether ketone (PEEK) material, a polyoxymethylene (POM) material, and a polyphenylsulfone material (PPSU).

8. A surgical stapling device comprising:
an elongate body defining a longitudinal axis, the elongate body having a proximal portion and a distal portion; and
a tool assembly supported on the distal portion of the elongate body, the tool assembly including an anvil assembly, a cartridge assembly, and a U-shaped frame, the U-shaped frame having a distal frame portion extending transverse to the longitudinal axis, a proximal frame portion extending transverse to the longitudinal axis, and a longitudinal frame portion extending between the distal frame portion and the proximal frame portion, the anvil assembly supported on the distal frame portion and including an anvil plate;
the cartridge assembly supported between the proximal frame portion and the distal frame portion and being movable in relation to the anvil assembly from a retracted position in which the cartridge assembly is spaced from the anvil assembly to an advanced position in which the cartridge assembly is in juxtaposed alignment with the anvil assembly, the cartridge assembly including a housing defining a cavity, a staple pusher positioned within the cavity, a knife holder positioned within the cavity, a knife supported on the knife holder, and an alignment pin, the knife including side edges, and a cutting edge that extends in a direction transverse to the longitudinal axis;
the alignment pin supported within the housing at a position spaced from the longitudinal frame portion, the alignment pin movable between a retracted position recessed within the housing and an advanced position extending from the housing into engagement with the anvil assembly;
wherein the tool assembly includes a guide plate supported on the longitudinal portion of the U-shaped frame, the guide plate having a guide surface including a distal portion that is angled inwardly away from the longitudinal portion of the U-shaped frame towards the alignment pin, wherein a first side edge of the side edges of the knife is positioned to move along the guide surface of the guide plate such that engagement of the first side edge of the knife with the distal portion of the guide surface of the guide plate compresses the first side edge of the knife.

9. The surgical stapling device of claim 8, further including a handle assembly, wherein the elongate body extends distally from the handle assembly.

10. The surgical stapling apparatus of claim 8, wherein the anvil assembly includes an anvil plate and a cutting plate supported on the distal frame portion of the U-shaped frame of the tool assembly, the anvil plate positioned to receive and deform the staples and the cutting plate positioned to engage the knife.

11. The surgical stapling device of claim 10, wherein cutting plate is sandwiched between the distal frame portion and the anvil plate, the anvil plate defining a knife slot to facilitate passage of the knife through the anvil plate.

12. The surgical stapling device of claim 10, wherein the cutting plate is formed from a plastic material selected from the group consisting of a polyether ether ketone (PEEK) material, a polyoxymethylene (POM) material, and a polyphenylsulfone material (PPSU).

13. A tool assembly comprising:
a frame having a distal frame portion, a proximal frame portion spaced from the distal frame portion, and a longitudinal frame portion connecting the distal frame portion to the proximal frame portion, the longitudinal frame portion defining a first axis and the proximal frame portion and the distal frame portion extending in a direction transverse to the first axis;

an anvil supported on the distal frame portion; and a cartridge assembly supported between the distal frame portion and the proximal frame portion, the cartridge assembly including a housing defining a cavity, a knife positioned within the cavity and movable along a knife path from a knife retracted position to a knife advanced position, and an alignment pin that is movable between a pin retracted position in which the alignment pin is recessed within the housing and a pin advanced position in which the alignment pin extends from the housing into engagement with the anvil, the knife including side edges and a distal cutting edge that extends in a direction transverse to the first axis, wherein the alignment pin is supported within the housing of the cartridge assembly at a position spaced from the longitudinal frame portion and includes a first guide surface that is positioned to engage a first side edge of the side edges of the knife as the knife moves from the knife retracted position towards the knife advanced position, the first guide surface of the alignment pin having a first distal guide portion that is angled towards the longitudinal portion of the frame into the knife path when the alignment pin is in the pin advanced position, wherein the first distal guide portion of the first guide surface is configured to compress the first side edge of the knife when the knife moves to the knife advanced position.

14. The tool assembly of claim 13, further including a guide plate supported on the longitudinal portion of the frame, the guide plate having a second guide surface including a second distal guide portion that is angled inwardly away from the first axis into the knife path, wherein a second side edge of the side edges of the knife is positioned to move along the second guide surface of the guide plate such that engagement of the second side edge of the knife with the second distal guide portion of the second guide surface of the guide plate compresses the second side edge of the knife.

15. The tool assembly of claim 14, wherein the knife has a first wing on the first side edge of the knife and a second wing on the second side edge of the knife, the first wing positioned to engage the first guide surface and the second wing positioned to engage the second guide surface.

16. The tool assembly of claim 13, wherein the housing defines a knife slot and staple receiving pockets positioned on opposite sides of the knife slot, and the cartridge assembly further includes a staple pusher positioned within the cavity and staples supported within the staple receiving pockets, the pusher movable from a pusher retracted position to a pusher advanced position to eject the staples from the housing.

17. The tool assembly of claim 16, wherein the anvil includes an anvil plate and a cutting plate supported on the distal frame portion of the frame, the anvil plate positioned to receive and deform the staples and the cutting plate positioned to engage the knife.

18. The tool assembly of claim 17, wherein the knife moves through the knife slot of the housing when the knife moves from the knife retracted position to the knife advanced position.

19. The tool assembly of claim 13, wherein the cartridge assembly includes a knife holder that is movable within the cavity of the housing, the knife secured to the knife holder.

20. The tool assembly of claim 17, wherein the cutting plate is formed from a plastic material selected from the group consisting of a polyether ether ketone (PEEK) material, a polyoxymethylene (POM) material, and a polyphenylsulfone material (PPSU).

\* \* \* \* \*